(12) United States Patent
Broeng et al.

(10) Patent No.: US 6,539,155 B1
(45) Date of Patent: Mar. 25, 2003

(54) MICROSTRUCTURED OPTICAL FIBRES

(76) Inventors: Jes Broeng, Nørgaardsvej 22B, 1.tv, DK-2800 Lyngby (DK); Stig Eigil Barkou, Lyngbyvej 431 B, 1.tv., DK-2820 Gentofte (DK); Anders Overgaard Bjarklev, Ørebjergvej 5, Gundsørnagle, DK-4000 Roskilde (DK)

( * ) Notice: Subject to any disclaimer, the term of this patent is extended or adjusted under 35 U.S.C. 154(b) by 0 days.

(21) Appl. No.: 09/719,132
(22) PCT Filed: May 21, 1999
(86) PCT No.: PCT/DK99/00279
§ 371 (c)(1),
(2), (4) Date: Dec. 8, 2000
(87) PCT Pub. No.: WO99/64903
PCT Pub. Date: Dec. 16, 1999

(30) Foreign Application Priority Data

Jun. 9, 1998 (DK) ........................................ 1998 00779

(51) Int. Cl.⁷ ................................................ G02B 6/20
(52) U.S. Cl. ...................................................... 385/125
(58) Field of Search ................................. 385/123, 124, 385/125, 126, 127, 147; 65/385, 428, 435

(56) References Cited

U.S. PATENT DOCUMENTS

| 5,802,236 A | 9/1998 | DiGiovanni et al. | 385/127 |
| 6,404,966 B1 | 6/2002 | Kawanishi et al. | 385/125 |

FOREIGN PATENT DOCUMENTS

| EP | 0 810 453 A1 | 12/1997 | G02B/6/12 |
| EP | 0 905 834 A2 | 3/1999 | |
| WO | WO 99/00685 | 1/1999 | G02B/6/16 |

OTHER PUBLICATIONS

Knight et al, "Photonic crystals as optical fibres—physics and applications", *Optical Materials* 11 (1999) pp 143–151.
Birks et al, "Full 2–D photonoci bandgaps in silica/air structures", *Electronics Letters*, vol. 31, No. 22, Oct. 26, 1995, pp. 1941–1943.
Knight et al, "All–silica–mode optical fiber with photonic crystal cladding: errata", *Optics Letters*, Vo. 22, No. 7, Apr. 1, 1997, pp. 484–485.
Broeng et al, "Highly increased photonic band gaps in silica/air structures", *Optics Communications*, 156, Nov. 15, 1998, pp. 240–244.
Barkou et al, "Silica–air photonic crystal fiber design that permits waveguiding by a true photonic bandgap effect", *Optics Letters*, vol. 24, No. 1, Jan. 1, 1999, pp. 46–48.
Barkou et al, "Dispersion properties of photonic bandgap guiding fibers", *Novel Fiber Structures (Cat. I)*, Feb. 26, 1999, pp. 117–119.

(List continued on next page.)

*Primary Examiner*—Akm E. Ullah

(57) ABSTRACT

The present invention relates to a new class of optical waveguides, in which waveguiding along one or more core regions is obtained through the application of the Photonic Bandgap (PBG) effect. The invention further relates to optimised two-dimensional lattice structures capable of providing complete PBGs, which reflects light incident from air or vacuum. Such structures may be used as cladding structures in optical fibers, where light is confined and thereby guided in a hollow core region. In addition, the present invention relates to designs for ultra low-loss PBG waveguiding structures, which are easy to manufacture. Finally, the present invention relates to a new fabrication technique, which allows easy manufacturing of preforms for photonic crystal fibers with large void filling fractions, as well as it allows a high flexibility in the design of the cladding and core structures.

91 Claims, 28 Drawing Sheets

OTHER PUBLICATIONS

Bjarklev et al, "Dispersion Properties of Photonic Crystal Fibres", *ECOC'98*, Sep. 1998, pp. 135–136.

Knight et al, "Pure Silica Single–Mode Fibre with Hexagonal Photonic Crystal Cladding", *OFC'96*, Feb. 29, 1996, pp. 1–4.

Knight et al, "All–silica single–mde optical fiber with photonic crystal cladding", *Optics Letters*, vol. 21, No. 19, Oct. 1, 1996, pp. 1547–1549.

Birks et al, "Endlessly single–mode photonic crystal fiber", *Optics Letters*, vol. 22, No. 13, Jul. 1, 1997, pp. 961–963.

Knight et al, "Large mode area photonic crystal fibre", *Electronics Letters*, vol. 32, No. 13, Jun. 25, 1998, p. 1347–.

Knight et al, "Properties of photonic crystal fiber and the effective index model", *J. Opt. Soc. Am. A*, vol. 15, No. 3, Mar. 1998, pp. 748–752.

Russell et al, "Silica/Air Photonic Crystal Fibres", *Proc. Int. Workshop on Silica Glasses Jpn. J. Appl. Phys.*, vol. 37 Supp. 37–1, 1998, pp. 45–48.

Knight et al, "Bragg scattering from an obliquely illuminated photonic crystal fiber", *Applied Optics*, vol. 37, No. 3, Jan. 20, 1998, pp. 449–452.

Birks et al, "2D Photonic Band Gap Structures in Fibre Form", *Photonic Band Gap Materials*, 1996, pp. 1–8.

Russell et al, "Photonic Crystal Fibres", *ECOC 97*, Conference Publication No. 448, Sep. 1997, p. 63.

Birks et al, "The analogy between photonic crystal fibres and step index fibres", *Novel Fiber Structures (Cat.I)*, Feb. 26, 1999, pp. 114–116.

Birks et al, "Single material fibres for dispersion compensation", *Novel Fiber Structures (Cat.I)*, Feb. 26, 1999, pp. 108–110.

Windeler et al, "Silica–Air Microstructured Fibers: Properties and Applications", *Novel Fiber Structures (Cat. I)*, Feb. 26, 1999, pp. 106–107.

Monro et al, "Efficient modelling of holey fibers", *Novel Fiber Structures (Cat. I)*, Feb. 26, 1999, pp. 111–113.

Ferrando et al, "Full–vector analysis of a realistic photonic crystal fiber", *Optics Letters*, vol. 24, No. 5, pp. 276–278, Mar. 1, 1999.

Ferrando et al, "Designing a photonic crystal fibre with flattened chromatic dispersion", *Electronic Letters*, vol. 35, No. 4, Feb. 18, 1999, (2 pages).

Gander et al, "Experimental measurement of group velocity dispersion in photonic crystal fibre", *Electronics Letters*, vol. 35, No. 1, Jan. 7, 1999, (2 pages).

Espindola et al, "External refractive index insensitive air––clad long period fibre grating", *Electronics Letters*, vol. 35, No. 4, Feb. 18, 1999, (2 pages).

Broeng et al, "Polarization properties of photonic bandgap fibers", *Center for Communications, Optics, and Materials (COM)*, ThG2–1–ThG2–4.

Monro et al, "Holey fibers with random cladding distributions", *Optics Letters*, vol. 25, No. 4, Feb. 15, 2000, pp. 206–208.

Broeng et al, "Analysis of air–guiding photonic bandgap fibers", *Optics Letters*, vol. 25, No. 2, Jan. 15, 2000, pp. 96–98.

Mogilevtsev et al, "Group–velocity dispersion in photonic crystal fibers", *Optics Letters*, vol. 23, No. 21, Nov. 1, 1998, pp. 1662–1664.

Knight et al, "Photonic Band Gap Guidance in Optical Fibers", *Science*, vol. 282, Nov. 20, 1998, pp. 1476–1478.

MICROSTRUCTURED OPTICAL FIBRES

FIELD OF INVENTION

The present invention relates to a novel group of cladding designs, especially for use in optical fibres, wherein a larger photonic bandgap may be obtained to confine light in hollow cores.

BACKGROUND OF THE INVENTION

Optical fibres and integrated optical waveguides are today applied in a wide range of applications within areas such as optical communications, sensor technology, spectroscopy, and medicine. These waveguides normally operate by guiding the electromagnetic field (the light or the photons) through a physical effect, which is known as total internal reflection. By using this fundamental effect, the propagation (or loss) of optical power in directions perpendicular to the waveguide axis is reduced.

In order to obtain total internal reflection in these waveguides, which are often fabricated from dielectric materials (in optical fibres) or semiconductors (in integrated optics), it is necessary to use a higher refractive index of the core compared to the refractive index of the surrounding cladding.

Today the preferred signal transmission medium over long and medium distances is the optical fibre, and total internal reflection is, consequently, a physical property, which has been known and used in technological development for decades. During the past ten years, however, the development within the area of new materials has opened up the possibilities of localisation of light or control of electromagnetic fields in cavities or waveguides by applying a completely new physical property—the so-called photonic bandgap (PBG) effect.

The PBG effect may be introduced by providing a spatially periodic lattice structure, in which the lattice dimensions and applied materials are chosen in such a way that electromagnetic field propagation is inhibited in certain frequency intervals and in certain directions. These PBG materials have been described in one-, two-, and three-dimensional cases in the scientific literature and in several patents (see for instance U.S. Pat. Nos. 5,386,215, 5,335,240, 5,440,421, 5,600,483, 5,172,267, 5,559,825).

A specific class of components, which makes use of such periodic dielectric structures, are the optical fibres (or waveguides), in which the periodic variation appears in directions perpendicular to the waveguide axes, whereas the structures are invariant along the waveguide axes.

Within recent years, especially researchers from University of Bath, UK, (see e.g. Birks et al., Electronics Letters, Vol.31 (22), p. 1941, October 1995) have presented optical fibres realised by having a core surrounded by thin, parallel, and air-filled voids/holes in a silica-background material, and organising the air-filled voids in a periodic structure in the cladding region of the fibres.

Although the above-cited Birks et al reference discloses the idea of photonic bandgap guiding fibers, it has since then been realised that the requirement that the cladding structure exhibits photonic bandgap effect is not necessary for these so-called microstructured fibers to be able to guide light (see e.g. Knight et al., Journal of the Optical Society of America, A., Vol.15 (3), p.748, March 1998). The reason for this is that microstructured fibers, which have a core region with a higher refractive index than the effective refractive index of the cladding structure, are able to guide light by total internal reflection. In accordance with this, it has also been realised that a periodic arrangement of the air voids is not a requirement for the operation of high-index core microstructured fibers (see e.g. U.S. Pat. No. 5,802,236).

It is important to notice that all of the high-index core microstructured fibers, which have been demonstrated, have not had an operation based on photonic bandgap effects. But simply due to the higher refractive index of the core region compared to the cladding (see e.g. U.S. Pat. No. 5,802,236 for definition of the core and cladding indices), all high-index core fibers have a fundamental mode which is guided due to total internal reflection (also known as index guiding).

In contrast to the high-index core fibers, low-index core fibers (i.e. fibres having a core region with a lower refractive index than the cladding) are not able to guide light leakage-free in the core region through total internal reflection. However, by designing a periodic cladding structure correctly, this cladding structure is able to exhibit photonic bandgap effects, as described in the above-cited Birks et al. reference.

Designing the cladding structure correctly involves optimising the periodic arrangement of voids with respect to sizes, dimensions, and morphology. Cladding structure which are exhibiting photonic bandgap effects are able to reflect light of certain wavelength and incident angles. This means that the cladding structure is able to confine light, which satisfies the condition that the light falls within a photonic bandgap, to a spatial region surrounded by the cladding structure. This is even the case when the spatial region has effectively a lower refractive index than the cladding structure. This is the operational principle of PBG guiding optical fibres and other PBG waveguides (see e.g. Barkou et al., Optics Letters, Vol.24 (1), p. 46, January 1999).

Due to the radically different physical mechanism causing the waveguidance, microstructured fibers classify into (at least) two groups. Namely those that are operating by photonic bandgap effect, which we will call PBG fibres (we will also refer to them as bandgap fibres or low-index core fibers), and those operating by total internal reflection, which we will refer to as high-index core fibres or index-guiding fibres.

Waveguidance by photonic bandgap effects are of significant future interest, as it allows radically new designs of optical fibres and other types waveguides. In particular for optical fibres, the core is not required to have a higher refractive index than the cladding. Such low-index core optical fibers (e.g. hollow core fibers) may be exploited in numerous applications, e.g. in sensor systems or for use as an ultra-low loss transmission fibre in telecommunication systems.

Recently the first photonic bandgap guiding optical fibre was demonstrated (see Knight et al., Science, Vol.282 (5393), p. 1476, November 1998). The design of this fibre was based on a Honeycomb arrangement of air voids in a silica background material in the cladding, and a single periodicity-breaking low-index region formed the core. The advantages of using a Honeycomb-based cladding structure compared to e.g. a triangular structure are that the cladding structure exhibits photonic bandgap effects for smaller (and thereby more realistic) air void sizes.

It is a disadvantage that, due to the triangular cladding structure, the PBG of the structures described by Birks et al. are not optimised for guiding electromagnetic radiation using the PBG effect.

It is a further disadvantage that the light in the recently demonstrated Honeycomb based PBG fibre is distributed almost entirely in silica.

It is a still further disadvantage that the cladding structure in the recently demonstrated Honeycomb-based PBG fibre is not optimised for guiding light inside a hollow core.

It is a still further disadvantage that the honeycomb arrangement of air voids in the cladding structure in the recently demonstrated PBG fibre is not optimised for obtaining a large void filling fraction.

It may be a problem or disadvantage of the present realisation of optical fibres with periodic dielectric cladding regions that careful, close-packed stacking of either hexagonal rods and hexagonal glass tubes (with central voids) or direct stacking of circular rods and thin circular tubes is required. These tubes and rods have been arranged in a close-packed triangular structure in a preform, where after the preform has been drawn into an optical fibre. Although these fibres according to the reports in the international literature show quite interesting and new optical properties, one of the disadvantages has been that the close-packing of the tubes and rods is not optimised for realising fibres with large void filling fractions.

As known to those skilled in the art large void filling fractions are required for obtaining PBG fibres where light is guided substantially inside a hollow core.

Thus, it is a further disadvantage that the present stacking of either hexagonal glass tubes (with central voids) or direct stacking of thin circular tubes in a close-packed structure is not optimised for fabricating optical fibres with large void filling fractions. U.S. Pat. No. 5,802,236 discloses microfabricated optical fibres having a core and a cladding region, wherein the cladding region comprises a multiplicity of spaced apart cladding features that are elongated in the direction of the fibre. The effective refractive index of the cladding region is less than the effective refractive index of the core region. Furthermore, the elongated features in the cladding are arranged in a non-periodic structure.

It is a disadvantage of the micro-fabricated optical fibre disclosed in U.S. Pat. No. 5,802,236 that due to the high-index core region the waveguiding characteristics are based on traditional total internal reflection of the electromagnetic radiation guided in the core region.

It is a further disadvantage of the micro-fabricated optical fibre disclosed in U.S. Pat. No. 5,802,236 that the non-periodic cladding structure will not be able to exhibit photonic bandgap effects. The non-periodic fibres disclosed in U.S. Pat. No. 5,802,236 will, therefore, only be able to guide light by traditional total internal reflection.

It is a further disadvantage for all high-index core fibres that these fibres will always support a fundamental mode which is guided due to total internal reflection. This naturally has the consequence that for applications within areas such as optical sensors and low-loss transmission links in telecommunications, where it may be of specific interest to be able to localise optical fields in a single, well-known mode-distribution within areas of low refractive indices (e.g. in vacuum, liquid- or gas-filled channels), the presently known high-index core fibres may not be used directly.

WO 99/00685 discloses a large core photonic crystal fibre (PCF) comprising a cladding having preferably a triangular periodic structure. The core region may be either a high-index or low-index region having a diameter of at least 5 $\mu$m. In a preferred embodiment, the fibre is guiding by total internal reflection, and has a solid core region made from pure, undoped silica and may be as large as 50 $\mu$m in diameter. With such a diameter, the fibre is capable of transmitting high powers, whilst maintaining sinlge-mode operation for sufficiently small air voids (see e.g. Knight et al., Electronics Letters, Vol.34 (13), p. 1347, June 1998). The reason for the single-mode operation is that the fibre in the preferred embodiment with a large solid silica core surrounded by a silica material with small air voids has a very little contrast between the effective refractive core index (equal to silica) and the effective cladding index. Thereby higher order modes can be avoided for this fibre configuration. It is again important to notice that the large core fibre with a high-index core is operating by traditional total internal reflection, and is therefore not able to confine light in a hollow core.

It is a disadvantage that the triangular cladding structure disclosed in WO 99/00685 are not optimised to provide a sufficient PBG effect so as to effectively confine visible or near-infrared electromagnetic radiation within a low-index core region of the fibre.

It is a further disadvantage of the structure disclosed in WO 99/00685 that in order to obtain a single-mode operation for the fibre with a large silica core, only very small air voids are allowed in the cladding. Thereby the fibre will have a very low contrast between the coreindex and the effective cladding index, which has the negative consequence that the guided mode(s) will not be strongly confined to the core region. The fibre will, therefore, be very sensitive to both micro- and macro-bends, and will experience losses under normal operation of e.g. fibres for telecommunications. The fibre, disclosed in WO 99/00685, is therefore not optimised for leakage-free transmission of high optical powers in a real environment.

It is an object of the present invention to provide a new class of optical waveguides, in which waveguiding along one or more core regions is obtained through the application of the PBG effect.

It is a further object of the present invention to provide optimised two-dimensional lattice structures capable of providing complete PBGs, which reflects light incident from air or vacuum. Such structures may be used as cladding structures in optical fibre, where light is confined and thereby guided in a hollow core region.

It is a still further object of the present invention to provide designs for ultra low-loss PBG waveguiding structures.

It is a still further object of the present invention to provide PBG structures, which are easy to manufacture.

It is a still further object of the present invention to provide a new fabrication technique, which allows easy manufacturing of photonic crystal fibers with large void filling fractions, as well as it allows a high flexibility in the design of the cladding and core structures.

SUMMARY OF THE INVENTION

For utilisation of PBG effects in optical fibres (as well as other types of waveguides and components) it is vital to be able to realise cladding structures which exhibit wide bandgaps as well as bandgaps which extend below the so-called air line. That the bandgaps extend below the air line means that the cladding structure is able to reflect light which is incident from air (or vacuum).

As known to those skilled in the art, the two main factors for obtaining these goals are realisation of structures with large void filling fractions, and proper design of the technique which does not only allow fabrication of fibres with larger void filling fractions than what is presently possible, but also greatly increases the flexibility of designing the morphology of the final fibre. Furthermore the present inventors have realised how to modify the size of the photonic bandgap of an optical fibre, in which the cladding structure is formed as two-dimensionally periodic low-index areas within a given material. If there in such a structure is defined a number of high-index areas, which are separated by the low-index areas forming the periodic structure, then the performance of the optical bandgap may be increased, if either the separation between these high-index areas, their respective refractive indices, or both are increased. The high-index areas couple via "bridging" areas between the low-index areas, and their separation may be obtained in a number of areas.

It is known from the international literature (Broeng et at., Optics Communications, Vol.156 (4–6), p. 240, November 1998) that it may decrease the size of the photonic bandgap, if interstitial voids are introduced in a triangular cladding structure of a photonic crystal fibre. For this reason, it would seem most reasonable to make a fibre design, which would tend to eliminate the interstitial voids if a triangular cladding structure is used.

However, the present inventors have realised that it is important where interstitial voids are placed, and they may indeed be advantageous, if they are located at places different from the immediately natural locations (the locations seen as a result of the prior art fabrication technique). As illustrated in the following description, the key point is to place the interstitial voids in such a manner that they further separate the high-index areas of the periodic cladding structure. The present invention not only includes a number of preferred embodiments for the positioning of the interstitial voids, it also includes a new fabrication technique making manufacturing of microstructured fibres with the desired positioning of the interstitial voids possible.

In the following, naturally a periodic structure will be defined by a primitive unit cell, as is the most widely used manner of simplifying the analysis of such a structure. It should be noted that many sizes of unit cells will exist but only one size of a primitive unit cell which is defined as a unit cell which has the smallest area (or volume for 3D periodic structures) possible and which, only by translation, may generate the structure. Naturally, a given periodic structure may have a plurality of primitive unit cells.

In the following, the structure is defined by a unit cell, which will be identical to a primitive unit cell.

In the present context, "positioned substantially along the line" will mean that it is desired to have elements positioned with centres directly on the connecting line between two adjacent primary elements, but that the manners of production will often alter this. In the prior art it is seen that the position of circular air voids (low-index areas) may be controlled to within 10% of the center-to-center distance between two adjacent primary elements, which is a sign of this substantial positioning.

Also, in the present context, the refractive index of the primary elements has to be lower than that of any material adjacent thereto, meaning that this actual change of index is the one providing the periodic structure. This step is not dependent on changes of refractive indices outside the immediate area around the circumference of the primary elements. Naturally, this step may be different for all primary elements, but usually the material adjacent to the primary elements is the same throughout the structure—and so is that of the primary elements, whereby the step will be the same at all circumferences around the primary elements.

In a first aspect, the present invention relates to an optical fibre with a waveguide structure having a longitudinal direction, said optical fibre comprising:
  a core region extending along the longitudinal direction,
  a cladding region extending along the longitudinal direction, said cladding region comprising an at least substantially two-dimensionally periodic structure comprising elongated elements each having a centre axis extending in the longitudinal direction of the waveguide, the elongated elements having a refractive index being lower than a refractive index of any material adjacent to the elongated elements,
  the periodic structure being, in a cross-section perpendicular to the longitudinal direction, defined by at least one unit cell, wherein, for each unit cell:
    any distance between centre axes of two neighbouring elongated elements does not exceed 2 $\mu$m, and
    the sum of all areas of all elements, which areas are comprised within a given unit cell, is larger than 0.15 times the area of that unit cell.

Dependent on the wavelength at which the optical fibre is intended to operate, the distance between centre axes of two neighbouring elongated elements may even become smaller than 1.9 $\mu$m, such as smaller than 1.8 $\mu$m, such as smaller than 1.6 $\mu$m, such as smaller than 1.4 $\mu$m, such as smaller than 1.2 $\mu$m, such as smaller than 1.0 $\mu$m, such as smaller than 0.8 $\mu$m, such as smaller than 0.6 $\mu$m.

For a given unit cell, the sum of all areas of all elements within the unit cell may preferable be larger than a constant times the area of that unit cell, said constant being larger than 0.2, such as larger than 0.25, such as larger than 0.3, such as larger than 0.4, such as larger than 0.5, such as larger than 0.6, such as larger than 0.7, such as larger than 0.8.

For each unit cell a first circle is defined as the largest circular area possible having a centre not positioned outside the unit cell and not enclosing any part of any elongated elements, and wherein the centres of those elongated elements, parts of which are within a distance of 1.5 or less, such as 1.2 or less, such as 1.1 or less times the radius of the first circle from the centre of the first circle, define the vertices of a polygon with three or more sides. The polygon may be a regular a triangular, rectangular, quadratic, or hexagonal polygon.

The optical fibre according to present invention may further comprising further, elongated elements each having a centre axis extending in the longitudinal direction of the waveguide.

These further, elongated elements have a refractive index being higher than a refractive index of any material adjacent to the secondary, elongated elements, and each having a centre not positioned outside the unit cell, and each having an area not exceeding the area of the unit cell.

Part of the further, elongated elements, in the cross-section, define a triangular structure, or a Honeycomb structure, or a Kagomé structure.

In the present context, a Honeycomb structure is defined as a hexagonal polygon, all sides of which are common to another hexagonal polygon. By a Kagomé structure is meant a structure defined by a hexagonal polygon and a regular triangle having a side length corresponding to that of the hexagonal polygon, and where hexagonal polygons exist, each side of which is common to a triangle.

The further, elongated elements, in the cross-section, are at least partly comprised within the first circle. Preferably, the centres of at least part of the further, elongated elements substantially coincide with the centre of the first circle.

In a second aspect, the present invention relates to an optical fibre with a waveguide structure having a longitudinal direction, said optical fibre comprising:

a core region extending along the longitudinal direction,
a cladding region extending along the longitudinal direction, said cladding region comprising an at least substantially two-dimensionally periodic structure comprising:
  primary, elongated elements each having a centre axis extending in the longitudinal direction of the waveguide, the primary elements having a refractive index being lower than a refractive index of any material adjacent to the primary elements,
  secondary, elongated elements each having a centre axis extending in the longitudinal direction of the waveguide, the secondary elements having a refractive index being lower than a refractive index of any material adjacent to the secondary elements,
  wherein any area of any primary element is larger than any area of any secondary element, and wherein
  the periodic structure being, in a cross-section perpendicular to the longitudinal direction, defined by at least one unit cell, wherein, for each unit cell:
  the sum of the areas of secondary elements, which areas are comprised within a given unit cell, is larger than 0.09 times the area of that unit cell.

Any area of any primary element is larger than a constant times any area of any secondary element, said constant being larger than 1.1, such as larger than 1.2, such as larger than 1.3, such as larger than 1.4, such as larger than 1.5, such as larger than 2, such as larger than 5, such as larger than 10, such as larger than 15, such as larger than 20, such as larger than 50.

To provide a large air filling factor, the sum of all areas of the secondary elements within the unit cell is larger than 0.1, such as larger than 0.15, such as larger than 0.2, such as larger than 0.25, such as larger than 0.3, such as larger than 0.4, such as larger than 0.5, such as larger than 0.6.

For each unit cell a first circle is defined as the largest circular area possible having a centre not positioned outside the unit cell and not enclosing any part of any primary, elongated elements, and wherein the centres of those primary, elongated elements, parts of which are within a distance of 1.5 or less, such as 1.2 or less, such as 1.1 or less times the radius of the first circle from the centre of the first circle, define the vertices of a first polygon with three or more sides.

The first polygon is a regular triangular polygon. At least part of the primary, elongated elements, in the cross section, define a triangular structure.

Preferably, none of the centres of the secondary, elongated elements, in the cross section, coincide with the centre of the first circle. The centres of at least part of the secondary, elongated elements, in the cross section, are positioned substantially along a line connecting the centres of two adjacent primary, elongated elements.

The optical fibre according to the present invention further comprises further, elongated elements each having a centre axis extending in the longitudinal direction of the waveguide, the further, elongated elements having a refractive index being higher than a refractive index of any material adjacent to the further, elongated elements, and each having a centre not positioned outside the unit cell, and each having an area not exceeding the area of the unit cell.

At least part of the further, elongated elements, in the cross-section, define a triangular structure, a Honeycomb structure, or a Kagomé structure. Definitions for the Honeycomb and Kagomé structure is given above.

The further, elongated elements are at least partly comprised within the first circle. Preferably, the centres of at least part of the further, elongated elements substantially coincide with the centre of the first circle.

For a given unit cell, the sum of all areas of primary elements within the unit cell is larger than a constant times the area of that unit cell, said constant being larger than 0.1, such as larger than 0.15, such as larger than 0.2, such as larger than 0.25, such as larger than 0.3, such as larger than 0.4, such as larger than 0.5, such as larger than 0.6, such as larger than 0.7, such as larger than 0.8.

In a third aspect the present invention relates to an optical fibre with a waveguide structure having a longitudinal direction, said optical fibre comprising:
  a core region extending along the longitudinal direction,
  a cladding region extending along the longitudinal direction, said cladding region comprising an at least substantially two-dimensionally periodic structure comprising:
    primary, elongated elements each having a centre axis extending in the longitudinal direction of the waveguide, the primary elements having a refractive index being lower than a refractive index of any material adjacent to the primary elements,
    secondary, elongated elements each having a centre axis extending in the longitudinal direction of the waveguide, the secondary elements having a refractive index being lower than a refractive index of any material adjacent to the primary elements,
    wherein any area of any primary element is larger than any area of any secondary element, and wherein, in a cross section perpendicular to the longitudinal direction the primary, elongated elements define a triangular structure,
    wherein the periodic structure being, in the cross-section, defined by at least one unit cell, wherein, for each unit cell:
    a first circle is defined as the largest circular area possible having a centre not positioned outside the unit cell and not enclosing any part of any primary, elongated elements, and wherein
    the centres of any of the secondary, elongated elements, in the cross section, do not coincide with the centre of the first circle.

Any area of any primary element is larger than a constant times any area of any secondary element, said constant being larger than 1.1, such as larger than 1.2, such as larger than 1.3, such as larger than 1.4, such as larger than 1.5, such as larger than 2, such as larger than 5, such as larger than 10, such as larger than 20, such as larger than 50, such as larger than 100, such as larger than 200, such as larger than 500.

For each unit cell the sum of all areas of the secondary elements within the unit cell is larger than 0.005 times the area of that unit cell, such as larger than 0.01, such as larger than 0.05, such as larger than 0.1 such as larger than 0.15, such as larger than 0.2, such as larger th an 0.25, such as larger than 0.3, such as larger than 0.4, such as larger than 0.5 times the area of that unit cell.

At least part of the secondary, elongated elements, in the cross-section, define a triangular structure, a Honeycomb structure, or a Kagomn structure. At least part of the secondary, elongated elements, in the cross section, have their centres positioned substantially along a line connecting the centres of two adjacent primary, elongated elements.

In the third aspect the fibre further comprises further, elongated elements each having a centre axis extending in the longitudinal direction of the waveguide, the further, elongated elements having a refractive index being higher than a refractive index of any material adjacent to the further, elongated elements, and each having a centre not positioned outside the unit cell, and each having an area not exceeding the area of the unit cell.

At least part of the further, elongated elements, in the cross-section, define a triangular structure, a Honeycomb structure, or a Kagomé structure.

The further, elongated elements, in the cross-section, are at least partly comprised within the first circle. Preferably, the centres of at least part of the further, elongated elements, in the cross section, substantially coincide with the centre of the first circle.

For a given unit cell, the sum of all areas of primary elements within the unit cell is larger than a constant times the area of that unit cell, said constant being larger than 0.1, such as larger than 0.15, such as larger than 0.2, such as larger than 0.25, such as larger than 0.3, such as larger than 0.4, such as larger than 0.5, such as larger than 0.6, such as larger than 0.7, such as larger than 0.8.

According to the third aspect of the present invention the material adjacent to the elongated elements have a refractive index larger than 1.0, such as larger than 1.2, such as larger than 1.3, such as larger than 1.4, such as larger than 1.45, such as larger than 1.5, such as larger than 1.75, such as larger than 2.0, such as larger than 2.5, such as larger than 3.0, such as larger than 3.5, such as larger than 4.0.

The material adjacent to the elongated elements may comprise silica-based materials. Alternatively or additionally, the material adjacent to the elongated elements may comprise polymer-based materials.

Those elongated elements having a refractive index being lower than a refractive index of any material adjacent to the elongated element have a refractive index equal to 1. Preferably, those elongated elements having a refractive index being lower than a refractive index of any material adjacent to the elongated element comprise a vacuum, a liquid or a gas.

Those elongated elements having a refractive index being higher than a refractive index of any material adjacent to the elongated element have a refractive index larger than 1.3, such as larger than 1.4, such as larger than 1.45, such as larger than 1.5, such as larger than 1.75, such as larger than 2.0, such as larger than 2.5, such as larger than 3.0, such as larger than 3.5, such as larger than 4.0.

Those elongated elements having a refractive index being higher than a refractive index of any material adjacent to the elongated element comprise doped silica.

The aspects of present the invention relate to specific cladding structures and comprise no limitations what so ever on the core region.

In fact, the present invention should be taken as one relating to these specific cladding regions for use in any type of optical fibre in combination with one or more cores or core regions of any type.

Normally, in relation to periodic dielectric structures, the core is taken as an area of the structure, where the periodicity of the structure is broken. The photonic bandgap structure is designed so as to make light transmission impossible, and an altering of the periodicity will, consequently, make light transmission possible—but only in the core and its close vicinity.

A number of different manners exist for defining the core. One manner is to replace one or more elements of the periodic structure with other elements with different refractive indices, cross sectional areas or shapes. Another manner is that the core has a periodic structure where only one or more elements are not present. Another manner is that the core also has a full periodic structure but this structure is different than the periodic structure of the cladding.

Preferably, the core region would comprise a first additional elongated element extending in the longitudinal direction of the fibre.

The core region may be defined as the smallest rectangular area comprising all elements breaking the symmetry of the at least substantially two-dimensionally periodic structure, the smallest rectangular area defining a first main axis and a second main axis, the first and second main axes having a first and a second length, respectively, the first length being equal to the second length.

Alternatively the core region may be defined as the smallest rectangular area comprising all elements breaking the symmetry of the at least substantially two-dimensionally periodic structure, the smallest rectangular area defining a first main axis and a second main axis, the first and second main axes having a first and a second length, respectively, the first length being larger than a constant times the second length, said constant being larger than 1.1, such as larger than 1.2, such as larger than 1.5, such as larger than 2, such as larger than 5, such as larger than 10, such as larger than 20, such as larger than 30, such as larger than 40, such as larger than 50.

An especially preferred first additional element is constituted by air, liquid or gas and being defined as a void in the material of the fibre, such as a void having a cross sectional area in the cross section being at least half the cross sectional area of the unit cell, such as at least one, such as at least 2, such as at least 3, such as at least 4, such as at least 5, such as at least 6, such as at least 7, such as at least 18, such as at least 36, such as at least 72 times the cross sectional area of the unit cell.

In that situation, the light may propagate almost entirely in a hollow core (e.g. containing a vacuum), which provides a number of advantages both for fibres used by the telecommunications industry as reduced propagation losses, improved dispersion properties and reduced non-linearities, and for fibres used in sensor applications, where e.g. a gas or liquid may be provided within the hollow core to obtain optimum overlap between the light and the gas or liquid.

In a number of different applications, the additional element or any material adjacent thereto may desirably comprise a dopant or a material showing higher order optical effects.

For communication purposes, higher order effects may be used for e.g. soliton communication.

For applications for fibre lasers or fibre amplifiers, the dopant may be e.g. a rare earth dopant adapted to receive pump radiation and amplify radiation travelling in the core region.

Alternatively, the dopant may be a light sensitive dopant, such as Germanium (e.g. loaded with other materials such as Ytterbium). In that situation, the dopant may be use for e.g. optically writing of a refractive-index grating in the fibre or core region.

For sensor applications, the dopant may be a material responsive to a characteristic of a gas or liquid, which response may be detected optically by light travelling in the core region.

In a number of applications, it is preferred that the core region comprises a second additional elongated element, the first and second additional elements being positioned at a distance where light travelling in one additional element is able to couple to the other additional element.

In one application, one elongated element may be a void holding a liquid or gas, which may be too turbid for light to travel through. In that situation, the light may travel in the other element while still coupling with the liquid or gas due to the limited distance between the elements.

In this situation, one may choose to have the liquid or gas travel only in one or both additional elements—or even in all elongated voids, such as voids of the cladding structure.

Also, by providing two elements between which the light may couple, a number of optical devices may be provided, such as optical fibre couplers. The optical coupling between core elements or core regions may be designed so as to have a predetermined coupling at one or more defined wavelengths, which further makes a number of optical elements possible.

Another possibility is to include elongated electrical conductors in the fibre structure, such as ultra thin metal cylinders. Hereby, performances such as poling of the optical material may be realised. This could be relevant for a large range of materials, e.g., in silica or polymer structures. These kind of additional elements may eventually result in the realisation of actively controlled optical waveguide components such as switching elements.

As indicated above, specific advantages will be obtained also when the second additional element is a low-index cylinder.

In fact, due to the periodic structure of the present fibre, the fibre may easily be made to comprise a plurality of core regions.

These core regions may be provided sufficiently close for light travelling in one core region being able to couple to one or more core regions.

Alternatively, the core regions may be positioned spaced apart in order to provide a number of separate waveguides in a single fibre. In fact, the waveguides may be spaced sufficiently apart in order for their respective photonic bandgap structures to be different and e.g. be optimised for different wavelengths or wavelength regimes.

Preferably, the core regions are positioned symmetrically within the periodic structure, a period of the core regions being larger than a period of the periodic structure.

Naturally, a fibre of the present type may be used for a number of applications, where fibres are already used today.

In a fourth aspect, the invention relates to a sensor for sensing or detecting at least one characteristic of a liquid or gas, the sensor comprising:
- a length of the optical fibre according to the invention, wherein the core region comprises at least a first additional element, the first element being a void extending along the longitudinal direction of the fibre,
- means for providing the liquid or gas into the void of the core region,
- means for introducing light into the core region, the light being adapted to interact with the gas or liquid in a manner so that the characteristic of the liquid or gas may be determined,
- means for detecting light emitted from the fibre and for determining the characteristic of the liquid or gas.

At present, the characteristic may be absorption, absorbance, the presence of a specific agent or material in the gas or liquid, such as for use as a smoke detector, or any other characteristic sensed by an optical sensing method.

If the gas or liquid has a sufficiently low absorption at the wavelength of the light, the introducing means may be adapted to introduce the light into the first additional element. In that situation, an optimum overlap exists between the light and the liquid or gas.

Alternatively, the core region may comprise a second, elongated element extending in the longitudinal direction of the fibre, where the first and second additional elements are positioned at a distance where light travelling in one additional element is able to couple to the other additional element, and wherein the introducing means are adapted to introduce the light into the second additional element. In that situation, the sensing takes place via the light extending from the second to the first element.

In another type of sensor, the characteristic may not be sensed directly by light. In that situation, it may be desired to expose a suitable material to the characteristic, where the response of that material may be sensed optically, Thus, in this situation, at least part of an inner surface of the first additional element may comprise a layer of a material being adapted to alter in response to the characteristic of the gas or liquid, and wherein the introducing means is adapted to introduce light of a wavelength responsive to the altering of the material.

Naturally, the sensor may additionally comprise means for providing the gas or liquid in the fibre, such as for repeatedly providing gas or liquid therein, such as a gas pump if the sensor is used as a smoke detector.

In a fifth aspect, the invention relates to a fibre amplifier for amplifying an optical signal, said fibre amplifier comprising:
- a length of optical fibre according to the invention, wherein the core region comprises a dopant material along at least part of the length, and
- means for providing pump radiation to the dopant material for pumping the dopant material so as to amplify the optical signal.

Normally, fibre amplifiers will, further comprise means for spectrally separating the amplified optical signal from the pump signal, in order not to have pump radiation travelling in the fibre outside the amplifying region.

Especially for communication purposes, the dopant would comprise rare earth tons, such as erbium, ytterbium, praseodymium, neodymium, etc.

For other purposes, such as if it is desired to optically write gratings or other structures in the fibre or core region, or simply for modifying the refractive index of the core region, the dopant may comprise a photosensitive material, such as germanium, caesium, and/or photosensitivity enhancing co-dopants (e.g., hydrogen or deuterium).

In a seventh aspect, the invention relates to a fibre laser for generation of laser radiation, said fibre laser comprising:
- a length of optical fibre according to any of the preceding claims, wherein the core region comprises a dopant material along at least part of the length,
- means for providing pump radiation to the dopant material for pumping the dopant material so as to amplify the optical signal, and
- feedback means for selectively feeding back at least part of the amplified optical signal so as to repeatedly pass the amplified optical signal through the length of the optical fibre so as to further amplify the optical signal.

Especially for communication purposes, the dopant comprises rare earth ions, such as Erbium, Ytterbium, Praseodymium, Neodymium, etc.

Also, the dopant may comprise a photosensitive material, such as germanium, in order to facilitate e.g. the writing of gratings in the fibre or core region—or for increasing the refractive index of the core region.

The present invention also applies to PBG structures in the case of planar optical components fabricated using materials such as semiconductors and/or dielectric materials. The PBG effect may be obtained through the formation of parallel air filled voids in a silica-based planar waveguiding structure.

One example of such a component could be obtained using plasma enhanced chemical vapour deposition (PECVD) methods, where those skilled in the art know that it is possible (and sometimes difficult to avoid) to form air cylinders, when high ridges are overcladded. It is, therefore, according to the present invention suggested to refine these fabricational properties by opening up larger air cylinders, and to combine their possible appearances with the periodicity needed to define photonic crystal structures in which the optical power is guided along the cylinder axes. These properties may be used in a single plane, where a two-dimensional PBG structure may be defined, or in a further development in the fabrication of multi-level air-cylinders opening the possibility of forming three-dimensional structures according to the previously outlined designs.

Also, it may be desired to dope the fibre material, such as the material adjacent to the elongated elements. Alternatively, a layer of a material may be desired along the length thereof. In that situation, at least one of the preform elements may be coated or doped with a predetermined material.

In a eighth aspect, the present invention relates to a preform for manufacturing an optical fibre, the preform having a length in a longitudinal direction and a cross section perpendicular thereto, the preform comprising:

primary, elongated elements each having a centre axis extending in the longitudinal direction of the preform, the primary elements having a length in the longitudinal direction being essentially the same as the length of the preform, inserted elements each extending in the longitudinal direction of the preform over a length being smaller than the length of the preform, the primary, elongated elements and the inserted elements form both a non-periodic structure and an at least substantially two-dimensionally periodic structure, the nonperiodic structure being surrounded by the substantially two-dimensionally periodic structure, the periodic structure being, in the cross-section perpendicular to the longitudinal direction, defined by at least one unit cell, wherein, for each unit cell:

a first circle is defined as the largest circular area possible having a centre not positioned outside the unit cell and not enclosing any part of any primary elements, the periphery of said first circle defining an inserted element.

The inserted elements, in at least part of the cross-section, defines a triangular structure. For each unit cell, the centres of those primary, elongated elements, parts of which are within a distance of 1.5 or less, such as 1.2 or less, such as 1.1 or less times the radius of the first circle from the centre of the first circle, define the vertices of a first polygon with three or more sides. The first polygon is a regular polygon.

Alternative, the first polygon has six or more sides, such as 12 or more, such as 18 or more, such as 36 or more.

The plurality of inserted elements are arranged along an axis extending in the longitudinal direction of the preform. At least part of the primary, elongated elements, in the cross-section, define a triangular structure, a Honeycomb structure, or a Kagomé structure. The outer surface of each of the primary, elongated elements may define a primary area, and the outer surface of each of the inserted elements may define a secondary area. The area of any primary area is different from any secondary area.

For each unit cell, the sum of all secondary areas is larger than 0.09 times the area of that unit cell, such as larger than 0.1, such as larger than 0.15, such as larger than 0.2, such as larger than 0.25, such as larger than 0.3, such as larger than 0.4, such as larger than 0.5, such as larger than 0.6, such as larger than 0.7, such as larger than 0.8 times the area of that unit cell.

In the preform any secondary area is larger than a constant times any primary area, said constant being larger than 1.1, such as larger than 1.2, such as larger than 1.3, such as larger than 1.4, such as larger than 1.5, such as larger than 2, such as larger than 4, such as larger than 7, such as larger than 10, such as larger than 20, such as larger than 50.

The primary, elongated elements may be hollow, whereas the inserted, elongated elements may be solid. The elongated elements may comprise silica-based materials. Alternatively, the elongated elements may comprise polymer-based materials.

The preform may further comprise further, elongated elements each having a centre axis extending in the longitudinal direction of the preform, and each having a centre not positioned outside the unit cell, and each having an area not exceeding the area of the unit cell, and each having a length in the longitudinal direction being essentially the same as the length of the preform, and each defining a further area being different from any area of primary, elongated elements. The further, elongated elements may be solid.

Regarding the position, the further, elongated elements are at least partly comprised within the first circle. Preferably, the centres of at least part of the further, elongated elements substantially coincide with the centre of the first circle.

The preform may further comprise a core region, the core region being defined as the non-periodic structure, the core region being surrounded by the at least substantially two-dimensionally periodic structure. Preferably, the core region comprises a hollow region, where the at least substantially two-dimensionally periodic structure surrounding the core region comprises at least two periods.

During the drawing process further initiatives may be employed to ensure large void filling fractions. This includes providing a gas in the voids of the fibre and sealing one end of the capillary tubes as disclosed in U.S. Pat. No. 5,802,236. Additionally for the present invention, it is preferred to seal the entire end of the preform by melting the jigs and the capillary (as well as any rods) together in one or both ends of the preform. Even sealing at specific locations along the preform may be of interest, if jigs are present at the specific locations. Alternatively, in a preferred embodiment only the voids not covering the high-index centres of the periodic cladding structure are sealed. Thereby the remainder of voids (those covering the high-index centres and therefore undesired) will collapse more rapidly than the voids which are desired to remain large.

Thus, in a ninth aspect, the present invention relates to a method for fabricating a preform, the preform having a length in a longitudinal direction and a cross section perpendicular thereto, the method comprising the steps of:

providing a holder for the preform, the holder having a predetermined shape and elongated grooves at its inner surface, the grooves having a length in the longitudinal direction being essentially the same as the length of the preform.

providing primary, elongated elements each having a centre axis extending in the longitudinal direction of the preform, the primary elements having a length in the longitudinal direction being essentially the same as the length of the preform, providing secondary elements each extending in the longitudinal direction over a length being smaller than the length of the preform, and positioning a plurality of secondary elements at essentially the same position along the longitudinal direction of the preform.

In a tenth aspect, the present invention relates to an optical fibre with a waveguide structure having a longitudinal direction, said optical fibre comprising:

a cladding region extending along the longitudinal direction, said cladding region comprising an at least substantially two-dimensionally periodic structure comprising elongated elements each having a centre axis extending in the longitudinal direction of the waveguide, the elongated elements having a refractive index being lower than a refractive index of any material adjacent to the elongated elements, a core region extending along the longitudinal direction, said core region comprising at least one void extending along the longitudinal direction, a cross sectional area of said at least one void being larger than a constant times a cross sectional area of any elongated elements comprised within the cladding region, said constant being larger than 1.1, such as 1.3, such as 1.5, such as 1.7, such as 2, such as 3, such as 5, such as 10, such as 20, such as 50.

The centre of the rectangle may be defined as the centre of the smallest rectangular area possible, the centre being positioned not outside the core region, the rectangle enclosing the at least one void, a rectangularity is defined as the length of the longest side of the rectangle divided by the length of the shortest side of the rectangle, a first axis is defined as a longest vertice possible, the centre of the rectangle being positioned on said first axis, wherein each end of said first axis is enclosed within one of the at least one voids, a second axis is defined substantially perpendicular to the first axis, the second axis being defined as a longest vertice possible, the centre of the rectangle being positioned on said second axis, wherein each end of said first axis is enclosed within one of the at least one voids, and a eccentricity is being defined as the length of the first axis divided by the length of the second axis.

The rectangle may be a square, wherein the eccentricity is larger than one, such as 1.1, such as 1.3, such as 1.5, such as 1.7, such as 2, such 3, such as 5, such as 10. The rectangularity may be larger than one, such as 1.1, such as 1.3, such as 1.5, such as 1.7, such as 2, such 3, such as 5, such as 10.

DETAILED DESCRIPTION OF THE INVENTION

The most basic requirement for waveguides to operate by PBG effects is that a periodic cladding structure exists and that this cladding structure is able to exhibit PBG effect. A well known structure to exhibit PBG effect is a regular triangular arrangement of large air voids in silica.

Figure 1:
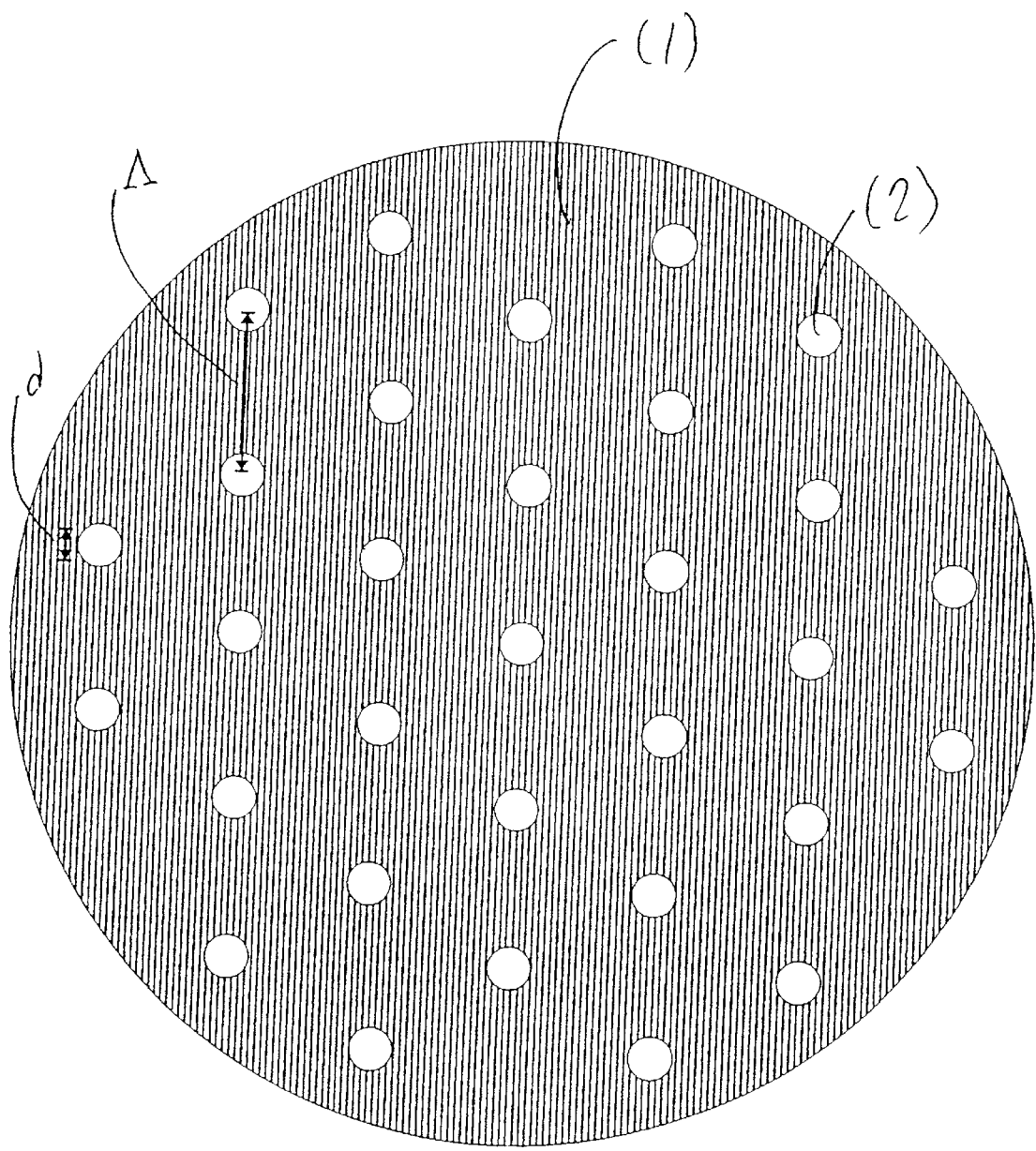
FIG. 1 shows a regular triangular photonic crystal structure, which is known as a cladding structure from the prior art of photonic crystal fibres.

In FIG. 1 a regular triangular structure is illustrated with indications of the background material (1), the voids/rods (2), the center-to-center spacing, $\Lambda$, between two adjacent voids/rods, and the diameter of a void/rod, d. A specific regular triangular structure of interest in optical fibres is the periodic arrangement of air voids in a silica background material. Such a structure is able to exhibit photonic bandgap effects as described by the above-cited Birks et al. reference. An important parameter when discussing micro structured fibers is the void filling fraction, f, of the cladding, which is defined as that fraction, in a cross-section perpendicular to the longitudinal fibre direction, of the total void area relative to the total cross-sectional area of the periodic part of the cladding. As the final fibres are considered invariant along the longitudinal direction, the above-defined filling fraction is equal to the total volume filling fraction of the void material in the periodic cladding structure.

Figure 2:
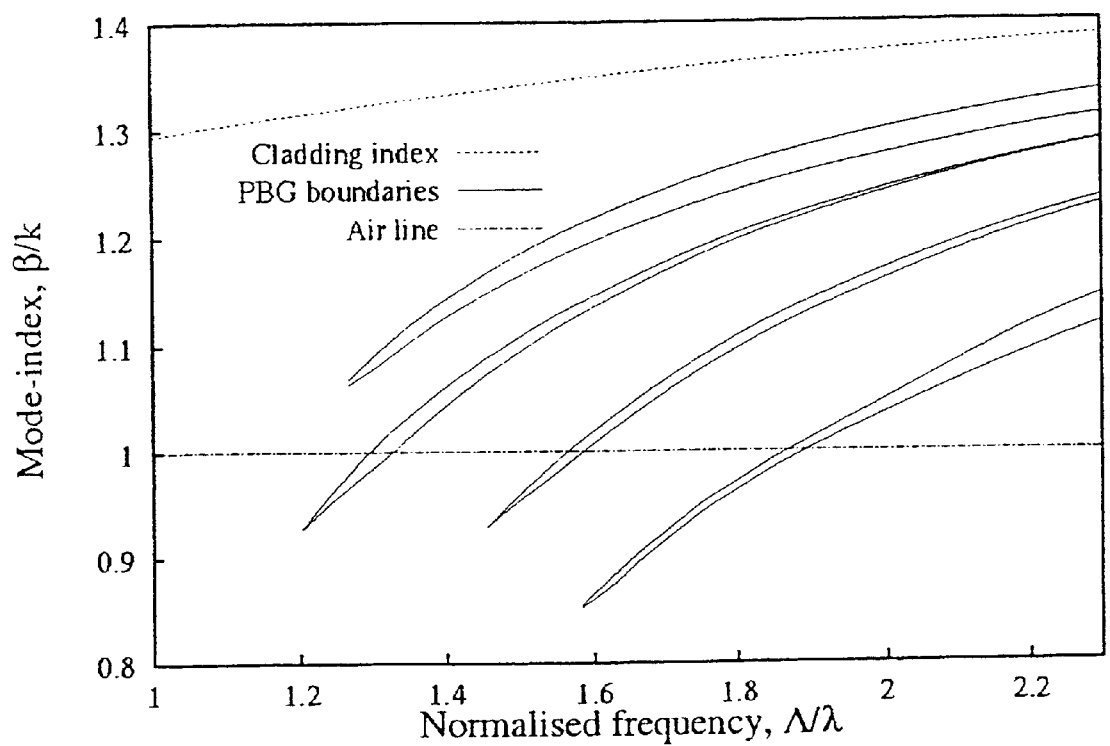
FIG. 2 shows a modal index analysis of a regular triangular photonic crystal structure with a relatively large air-filling fraction of 45%. The solid lines show the PBG boundaries within which no field solutions exist in the crystal. The line noted 'Effective cladding index' (dotted line) is defined as the lowest-frequency allowed mode in the periodic structure—and relates to the effective index, $n_{c,eff}$, of the cladding structure. The so-called air line is indicated by the dashed dotted line.

An illustration of the photonic bandgaps exhibited by a triangular arrangement of circular air voids in silica is presented in FIG. 2. The void filling fraction for this specific structure is 45% (equal to that presented in the Briks et al. reference). For the numerical simulation presented in FIG. 2 the refractive index of the silica background material was set to be equal to 1.45, and the refractive index of the voids was set equal to 1.0 (to simulate air or vacuum or vacuum voids).

The illustration shows an index analysis of the triangular photonic bandgap structure, where those skilled in the art will recognise that the index of an allowed mode within the structure is defined as the propagation constant, $\beta$, (which is defined as that component of the wave vect or which is parallel to the centre axis of the voids) divided by the wavenumber, k, of the allowed mode.

The simulation reveals four regions where no modes are allowed (indicated by the PBG boundaries). These four so-called complete, out-of-plane two-dimensional PBGs are exhibited solely due to the periodic nature of the triangular structure. Within the four PBG regions no modes are allowed for the triangular structure, and the triangular structure may hence be used to reflect electromagnetic radiation.

It is very important to notice that some of the PBG regions cross the so-called air-line, which indicates that the triangular structure is able to reflect electromagnetic radiation which is incident from air for the specific ranges of free-space wavelength, $\lambda$, and $\beta$ combinations where the PSG regions lie below or overlap the air line. As the frequencies are given in normalised units, where the center-to-center void spacing, $\Lambda$, has been used for the normalisation, it is clear that for the triangular structure to reflect visible and near-infrared light (wavelengths around 1 $\mu$m) which is incident from air, $\Lambda$-dimensions around 2 $\mu$m and smaller are required. Therefore, in order to fabricate an optical fibre, where an air filled core region is surrounded by a PBG structure reflecting light from air, the final fibre does not only need a large air filling fraction, but also needs very small dimensions.

Figure 3:
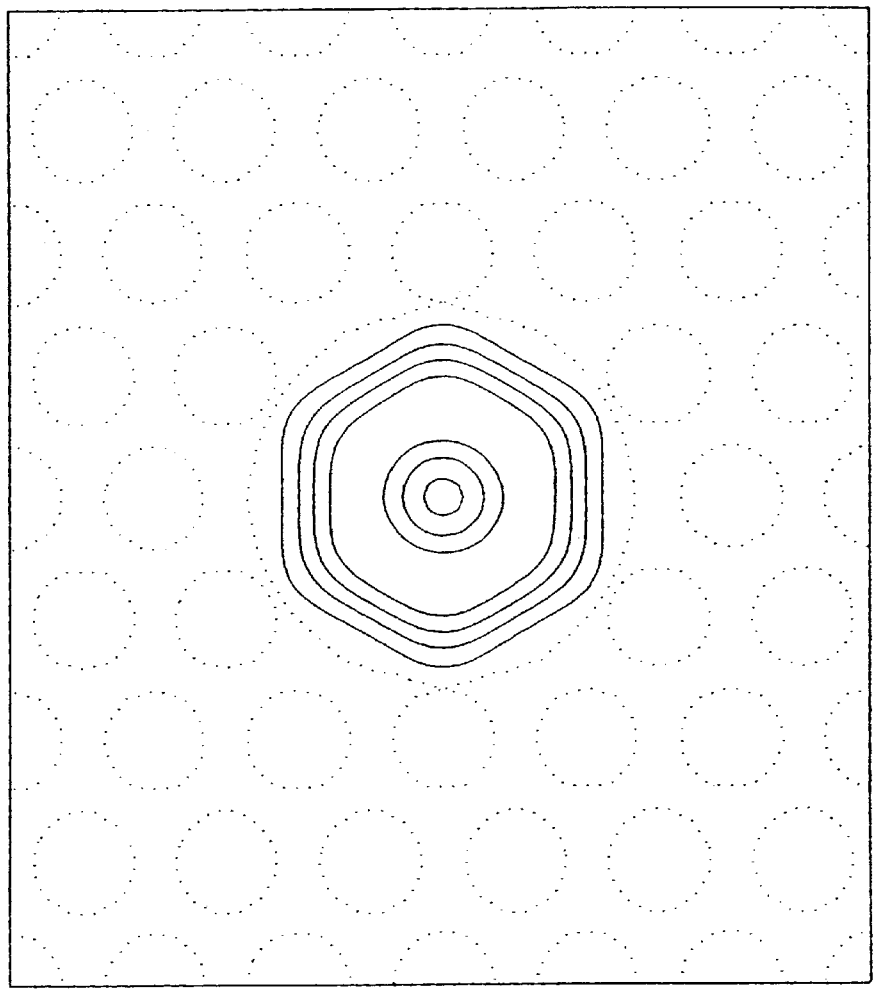
FIG. 3 shows a theoretical prediction of an air-guided mode in a photonic crystal fibre with a large air filling fraction in the cladding (f=45%), and an air (or vacuum) filled core with an area significantly larger than the area of a single cladding hole. The mode intensity peaks in a ring around the center of the core.

An example of a numerical simulation of a bandgap fibre which guides light entirely in a hollow core is presented in FIG. 3. The fibre has a regular triangular cladding structure which surrounds a large air (or vacuum) core. The fibre in FIG. 3 has a void filling fraction of 45%. If the fibre is to be operated around 1.5 $\mu$m, the required dimension of the cladding structure of the fibre is a center-to-center void spacing of 1.9 $\mu$m (the mode in FIG. 3 was calculated for normalised frequencies, and the mode appeared in the bandgap region in FIG. 2 around $\Lambda/\lambda$=1.3). Using the presently known fabrication techniques, it has not been possible to realise fibres with the required small dimensions (below 2 $\mu$m) which at the same time have large void filling fractions (well above 15%) in the cladding structure.

The present inventors have, however, realised that the presently used stacking of capillary tubes in a close-packed array does not represent the optimum fabrication technique for fabricating photonic crystal fibres with large void filling fractions. Instead of the presently used close-packing technique, the present inventors have realised a new fabrication technique, where robust fibres with very large void filling fractions even for small dimensions may be fabricated.

Figure 4:
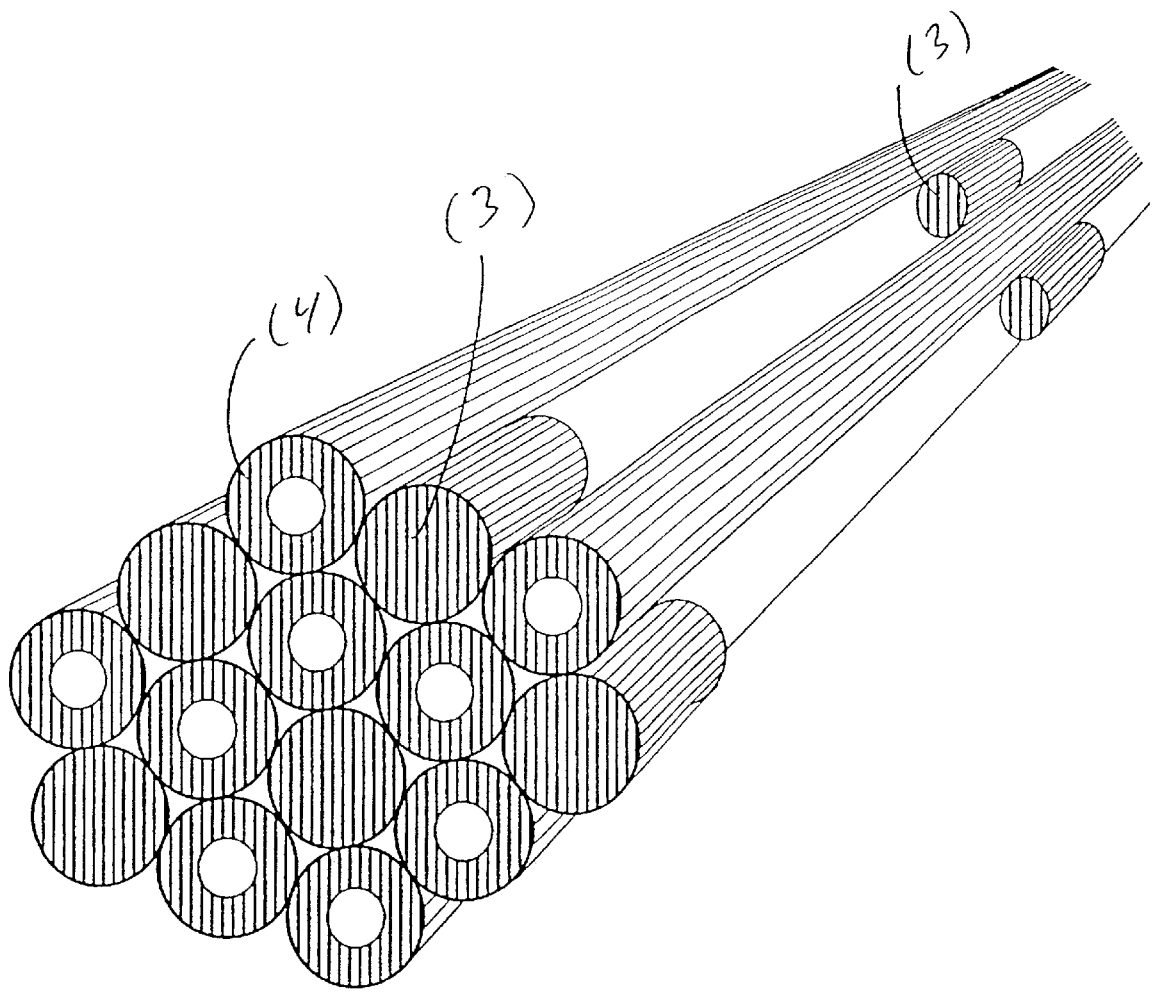
FIG. 4 illustrates the new fabrication technique, where short jigs are introduced in order to fabricate fibers with large void filling fractions. The jigs do not run the entire length of the preform.

The fabrication technique, which concerns mainly fabricating a new type of preform, is illustrated in FIG. 4. The fabrication technique utilises short jigs (3), which do not run the entire length of the preform, to support capillary tubes (4) in a non-close-packed array. Thereby fibres may be fabricated with larger void filling fractions than what is presently possible.

In a preferred embodiment the capillary tubes (4) are arranged in a Honeycomb structure (see FIG. 4), and the jigs (3) are arranged in a triangular structure. Since the jigs do not run the entire length of the preform, there will be (large) sections of the preform where in a cross-section the jigs are not present.

Figure 5:
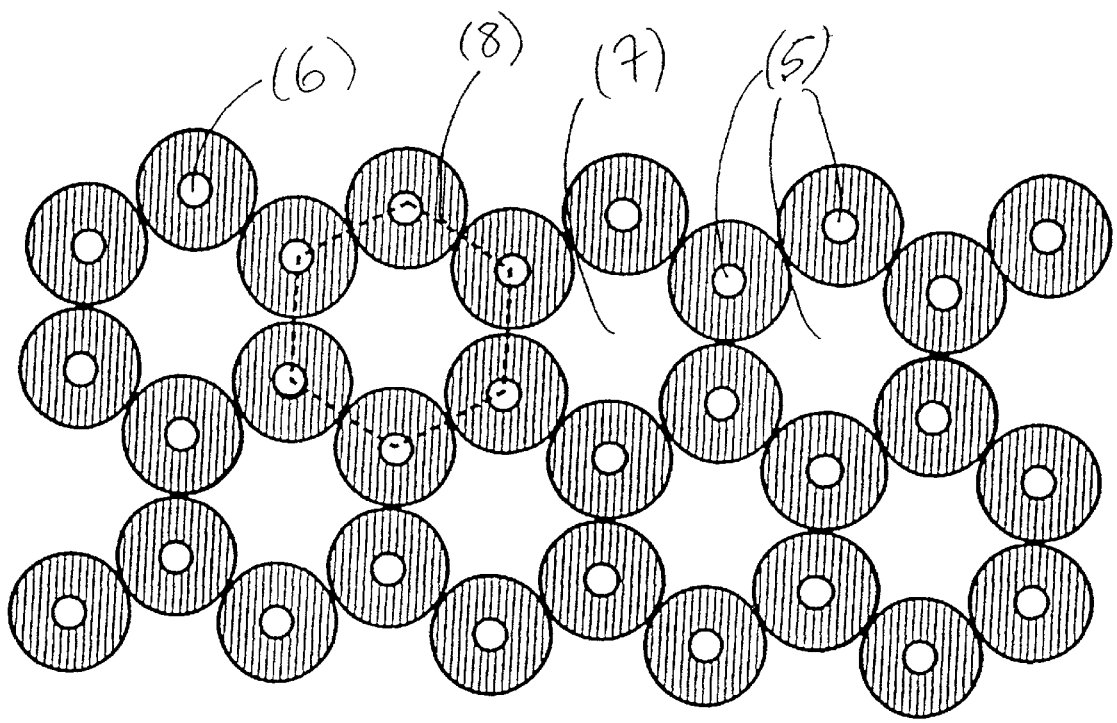
FIG. 5 illustrates a cross-sectional part of a preform realised using the new fabrication technique. The cross-section is illustrated at a position along the preform, where the jigs do not extend.

In FIG. 5 is illustrated such a cross-section for a preferred embodiment of the preform. As appears from FIG. 5, all the voids (5) without separating between the capillary-introduced voids (6) and jig-introduced voids (7)) are arranged in a triangular structure. A unit-cell of the structure is indicated (8). As also appears from FIG. 5, the size of the jig-introduced voids (7) are larger than the size of the capillary-introduced voids (6). This not only have the obvious effect that a larger total void filling fraction in the preform is achieved compared to the present fabrication technique, but also that a larger void filling fraction may be preserved in the final fibre. The reason for this relates to the surface tension forces, which are decreasing the size of the voids during the drawing/pulling of the preform to the final fibre.

Figure 6:
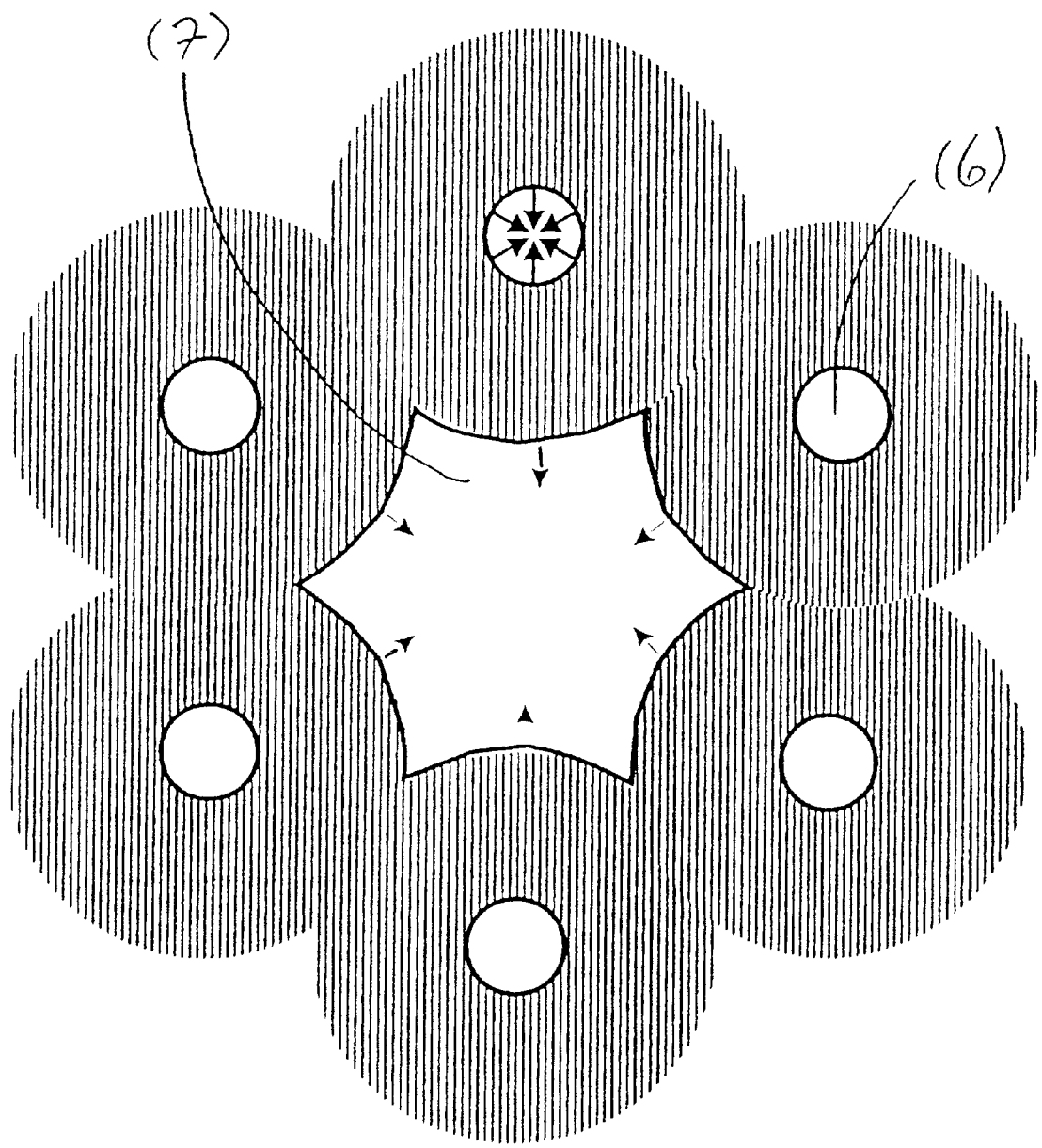
FIG. 6 illustrates the surface tension forces, which cause the voids to collapse during drawing/pulling of the preform to the final fibre.

Even total collapse of the voids during fabrication, which is often seen for fibres drawn to very small dimensions, may be avoided (or at least will take place for higher drawing/pulling temperatures). Since the surface tension forces are strongly dependent on the radii of the voids, where the forces increase very strongly with decreasing radius, the larger voids (7) (introduced through the new fabrication technique) experience weaker surface tension forces than the voids formed from the inner surface of the capillary tubes (6). The surface tension forces are indicated in FIG. 6.

To illustrate the advantage of the new fabrication technique over the presently used technique, the total void filling fraction in the cladding for two different fibres are compared. One of the fibres for the comparison (Fibre 1) is fabricated using the presently known technique (using a close-packed array of capillary tubes), and the other (Fibre 2) is fabricated using the new technique, where the capillary tubes are arranged in a Honeycomb structure (using jigs to support the tubes and create large voids). The capillary tubes used in both fibres are identical, but the Fibre 2 contains only two thirds of the number capillary tubes of Fibre 1. The total void filling fraction in Fibre 1, $f_{T,1}$, during the drawing/pulling process may as a first approximation be written as $$f_{T,1} = x(t) \cdot f_{i,1}, \quad (1)$$

where $f_{i,1}$ is the initial void filing fraction in the fibre, and $x(t)$ describes the decrease of the void size as a function of temperature. Since the silica is becoming more fluent for increased temperature (which is needed in order to draw/pull the preform to small dimensions), the surface tension forces will cause a decrease in size of the void for increased temperature. For the Fibre 2, in which only two thirds of the voids are identical to the voids in Fibre 1, and one third of the voids are larger, the total void filling fraction, $f_{T,2}$, may as a first approximation be written as $$f_{T,2} = 2/3 \cdot x(t) \cdot f_{i,1} + y(t) \cdot f_{i,2}(t), \quad (2)$$

where $f_{i,2}$ is the initial void filing fraction of the jig-introduced voids, and $y(t)$ describes the decrease of the jig-introduced void size as a function of temperature. The factors $x(t)$ and $y(t)$ will in general not be identical due to the fact that the two types of voids will have different shapes, and therefore will experience different surface tension forces.

An important advantage, resulting from the new fabrication technique, is that the jig-introduced voids (7) for the Fibre 2 will tend to open up (or at least their decrease in size will be significantly hindered), as the surface tension forces initially decrease the size of capillary-introduced voids (6). The stronger surface tension forces for the capillary-introduced voids, compared to the jig-introduced forces, will thus have the effect that the x(f)-factor initially will decrease faster than the y(t)-factor.

Figure 7:
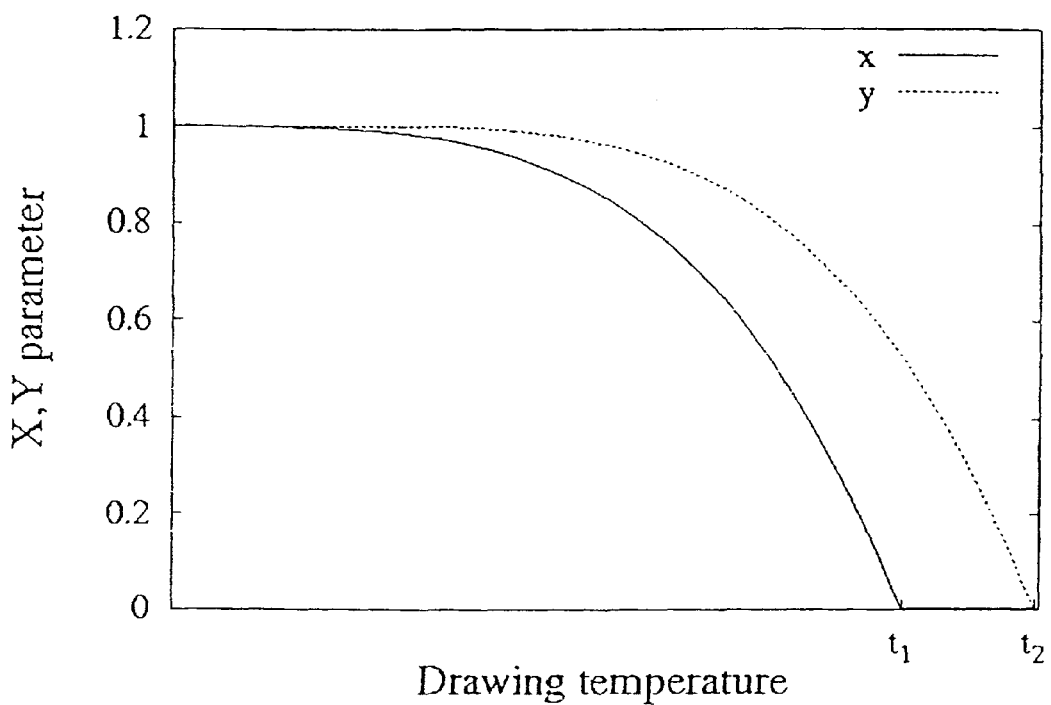
FIG. 7 shows an example of the temperature dependence of the x- and y-parameters, which are used theoretically to describe the collapse of the voids during drawing/pulling of the preform.

The above-described tendency is illustrated in FIG. 7, where a simple simulation of the collapsing of the capillary-introduced and jig-introduced voids has been performed. The figure reveals an important advantage of the new fabrication technique, namely that the size of the jig-introduced voids may be maintained for higher drawing/pulling temperatures than the capillary tube-introduced voids. This is seen as the broader temperature region for which $y(t)$ is approximately equal to one, compared to that of $x(t)$.

That the jig-introduced voids, furthermore, initially are larger than the capillary-introduced voids naturally means that the total void filling fraction for a fibre realised using the new fabrication technique (Fibre 2), will be larger than the total void filling fraction of a 'usual' fibre (Fibre 1).

Figure 8:
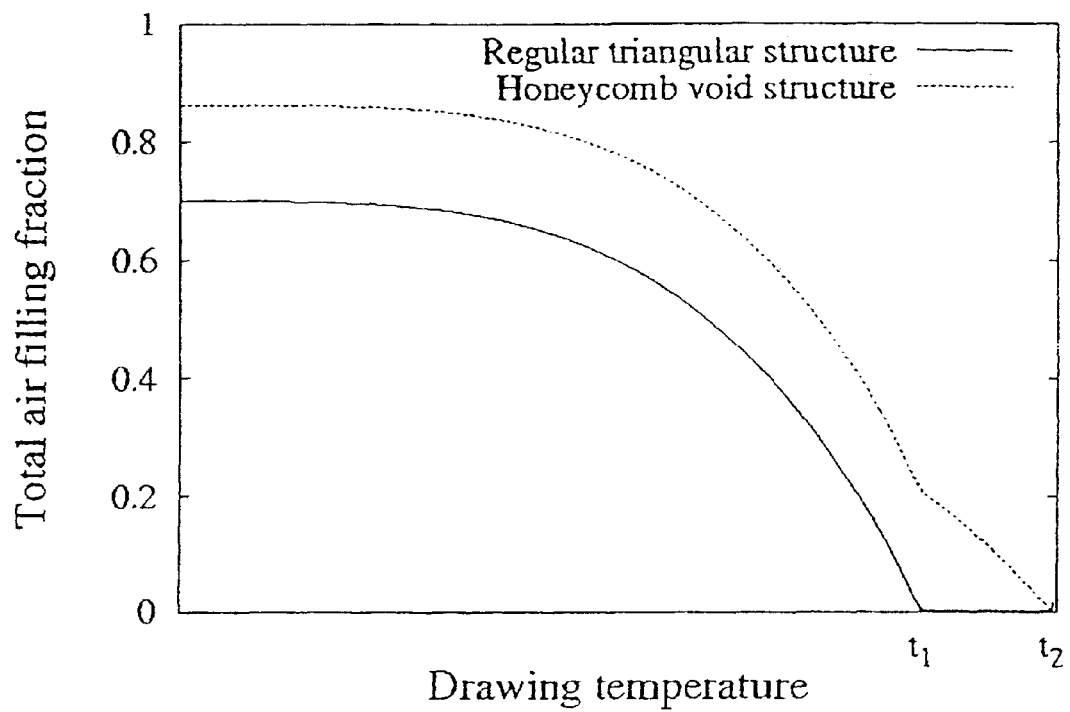
FIG. 8 shows an example of a simple simulation of the total void filling fraction for an optical fibre fabricated using the prior art fabrication technique (dotted line), and the total void filing fraction for a fibre fabricated using the new fabrication technique disclosed in this application (solid line).

The total void filing fraction of the two fibres have been illustrated in FIG. 8, where an initial void filing fraction of 70% has been used for the capillary-introduced voids ($f_{T,1}$=0.70), and an initial void filling fraction of 40% for the jig-introduced voids ($f_{T,2}$=0.40). The figure shows two significant advantages for fibres realised using the new fabrication technique. Firstly, the total void filling fraction, which may be obtained at a given drawing/pulling temperature is larger. As the drawing/pulling temperature is the most important factor for realising fibres with small dimensions (higher temperatures means that the fibre may be drawn/pulled to smaller dimensions), this first advantage is crucial for fabricating microstructured fibres with large void filling fractions for small fibre dimensions. Secondly, the critical temperature at which the voids are collapsed (the void filling fraction is reduced to zero) is seen to be increased as a result of the new fabrication technique ($t_2 > t_1$). This increased temperature range, in which the fibre may be fabricated, means that if a certain void filling fraction is desired for the final fibre, then the fibre may be fabricated at a higher temperature using the new fabrication technique.

The new fabrication technique, therefore, not only allows fabrication of fibres with larger void filling fractions than what is presently possible, it further provides the very important possibility of manufacturing the fibres at higher temperatures—without total collapse of the voids. To be able to manufacture the fibres at higher temperatures offers a more easy fabrication of the fibres, as well as a higher degree of uniformity along the centre axis of the fibres. These benefits may be crucial for commercial exploration of the fibres as the easier fabrication and increased uniformity mean a better reproducibility of the fibres. Also for the important aspect of surface roughness, which may cause serious scattering losses in the fibres, the possibility of fabricating the fibres at higher temperatures allows realisation of smoother boundaries between the voids and the background material, which thereby reduces the scattering losses.

So far the detailed description of the invention has mainly concerned the properties of the cladding structures of bandgap guiding optical fibres. Following this, will be presented a discussion of the core region(s), as the optimisation of the cladding structures is strongly dependent on which specific cores are of interest. For the present invention, these cores are hollow containing preferably air, another gas, a liquid or a vacuum.

By locally breaking the periodicity of a photonic crystal, a spatial region with optical properties different from the surrounding bulk photonic crystal can be created. If such a defect region supports modes with frequencies falling inside the forbidden gap of the surrounding full-periodic structure, these modes will be strongly confined to the defect, which thereby forms the core of the waveguide. This is the principle on which the operation of the PBG guiding fibres relies, namely a complete out-of-plane 2D bandgap exhibited by the photonic crystal cladding, and a correctly designed defect, forming a spatial region to which very strong transverse confinement can be achieved. For this defect region to exhibit optical properties different from the surrounding periodic structure (i.e., be able to support a localised mode), it is important to notice that it is not a requirement that the defect region has a higher index than its surroundings.

For a non-periodic dielectric surrounding media the only case under which field localisation can occur is for a high-index core region (which is of course the case of total internal reflection utilised in all conventional optical waveguides). Leakage-free guidance of light confined to a region with a lower refractive index than its surroundings would, therefore, not be expected to be possible from index guidance waveguide theory, but if the surrounding material exhibits PBG effects even a low-index defect region may be able to localise the light, and thereby act as a (new) highly unusual waveguide.

A numerical simulation of a microstructured fibre with a triangular cladding structure as that of FIG. 2 and a large hollow core (with a refractive index equal to air) has already been presented in FIG. 3. The figure illustrates the distribution of the square of the electric field for a guided mode, which is localised mainly in air (or vacuum). The fibre has a void filling fraction of 45% in the cladding, and a core size corresponding to approximately 14 times the size of a single void in the cladding. Contours of the central part of the fibre structure (including the core) are indicated by the dotted lines. The confined mode was found localised to the core defect for a $(\lambda,\beta)$ value falling inside the photonic bandgap region at a normalised frequency of approximately 1.3 $\Lambda/\lambda$.

From FIG. 2 it is seen that such a value falls within the range where one of the photonic bandgaps overlaps the air-line. Therefore light with the specific $(\lambda,\beta)$ value is not allowed in the cladding structure, but may be reflected if incident from air. This is in agreement with the numerically found mode, for which the light is almost entirely localised within the hollow core. As the mode is not allowed to couple to modes in the cladding (since it falls within the photonic bandgap), the mode will experience leakage-free guidance through the fibre. Such a property, namely leakage-free guidance of light in a hollow core fibre is of tremendous interest for a series of application, for which the sensors and telecommunications areas have already been discussed. In the ideal situation, where the field is entirely confined in the hollow core of fibre, and this hollow core is a vacuum or a gas with a low absorption, the propagation loss of the mode in FIG. 3 may clearly be ultra low.

Even in less ideal situations where the field is only partly located in the hollow core, the absorption loss will at least be lower than that of the cladding background material (e.g. pure silica). The fundamental barriers for low-loss guidance in traditional total internal reflection guiding fibres (i.e. high-index core fibres) may therefore obviously be broken by the emergence of fibres guiding light in hollow cores. That the field may be confined in a hollow core has many further advantages, among these being that high intensities may be transmitted through the fibre without out damaging the fibre background material. Thereby much higher power may be transmitted in a PBG guiding optical fiber with a hollow core, compared to any high-index core fiber. A further advantage concerns the elimination of non-linear effects in the optical fibre, which set ultimate limits on the speed at which data may be transmitted through conventional optical fibres. If the hollow core is a near-vacuum or just pure air practically no non-linear effects will take place in the fibre (for practically any power level). Finally material dispersion is almost negligible if the hollow core comprises a vacuum.

As the exhibition of PBG effects is a fundamental requirement for PBG based waveguides, it is naturally necessary first of all to provide designs for cladding structures that are able to exhibit PBG effects. Furthermore it is important to optimise the cladding structures so as to both increase the width and extend of the PBG regions. Compared to presently known fibres, the present invention discloses a number of improved cladding structures, which provides wider photonic bandgaps that extend below the air line. As those skilled in the art will recognise, structures exhibiting wider bandgaps allow a stronger confinement of a localised mode within the core region. As a stronger confinement results in a more robust and bend insensitive fibre, new cladding structures optimised for wide bandgaps are naturally of significant importance for future realisation of ultra low-loss PBG guiding fibres. As the 'tuning'-ranges of the fibres (i.e. the wavelength range in which the PBG guiding fibre may be operated) furthermore are directly related to the width of the bandgaps, the importance of optimising the cladding structures is further underlined.

The above discussion can be summarised by stating that for the realisation of optical fibers with light-guidance in hollow cores, there are two main issues to be addressed for the cladding structures, namely firstly fabricating periodic cladding structures with small dimensions as well as with large void filling fractions and secondly optimising the morphology of periodic cladding structure.

Figure 9:
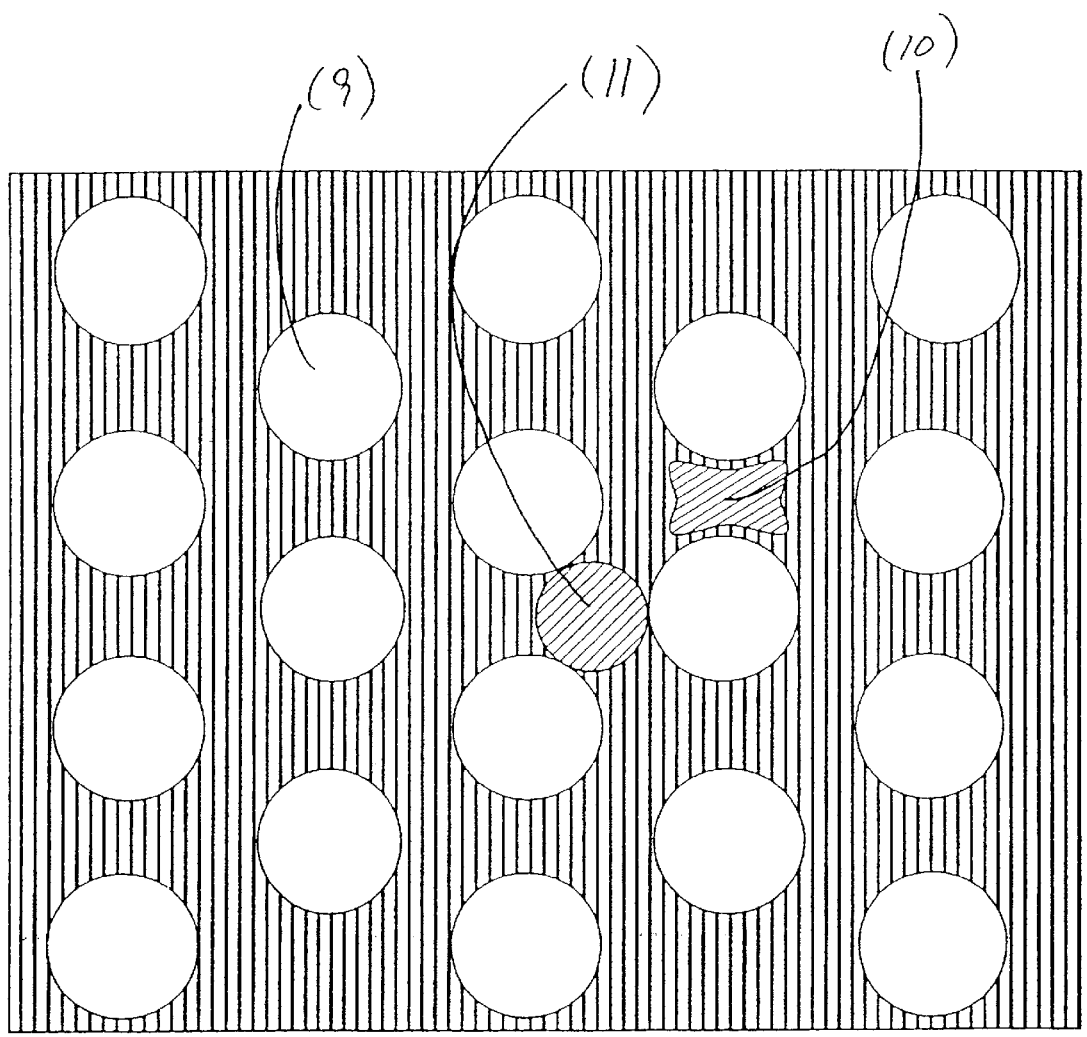
FIG. 9 illustrates the concept of nodes and veins used for the optimisation procedure of the cladding structures.

The present inventors have realised a design route for optimising the morphology of the periodic cladding structures, and to illustrate the design route to the improved cladding structures, a concept of high-index regions (nodes) connected by bridging areas (veins) will be introduced. Using this concept, the regular triangular photonic crystal may be regarded as a structure where the nodes are the regions between three adjacent voids, and the regions bridging two nodes is denoted veins (i.e. a vein is the region between two adjacent voids in the regular triangular structure). For the regular triangular structure the low-index voids (9), the nodes (10) and the veins (11) are indicated in FIG. 9.

To optimised a given cladding structure it is of importance to analyse the impact on the width and extend of the bandgaps by introducing additional elements in a basic structure. As will here be demonstrated, such an analysis supports the design-route taken by the present inventors for optimising photonic crystals structures. Basis is taken in the triangular structure with a void filling fraction of 45%.

Figure 10:
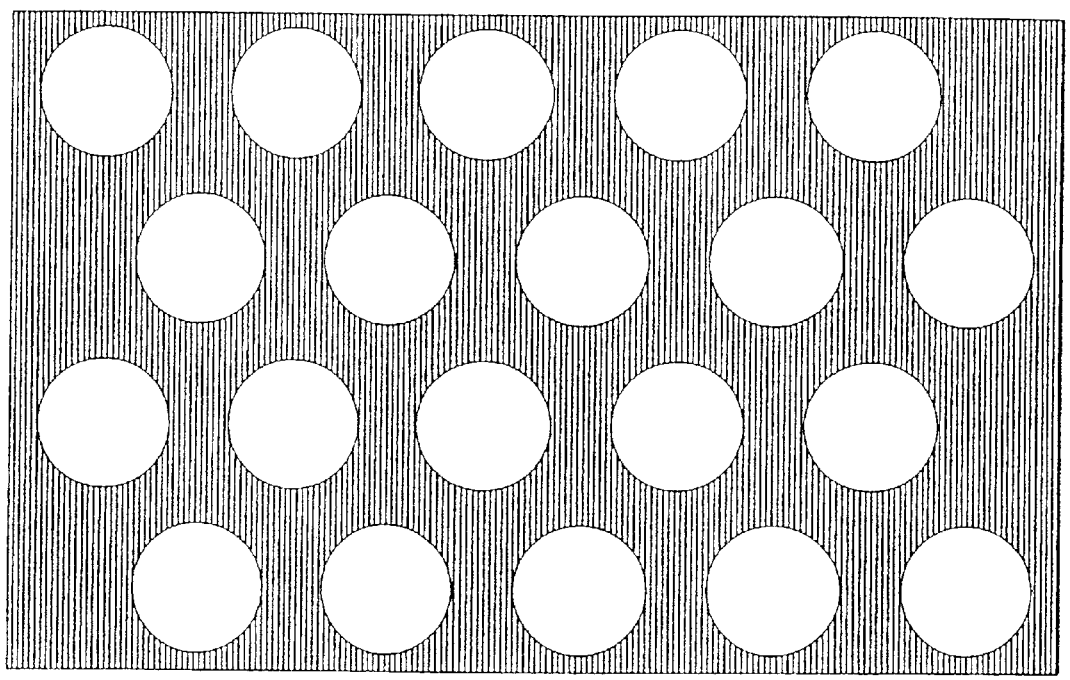
FIG. 10 shows a basic triangular structure.

The structure is schematically illustrated in FIG. 10 (the modal index analysis presented in FIG. 2 is for this structure). Next, will be focused on the influence on modifications to the basic structure by analysing the bandgap which overlaps the air line at the highest frequencies in FIG. 2. This bandgap is chosen for the analysis, since this bandgap is the one (of the four) which overlaps the air line for the largest structure dimensions, and will therefore be the easiest to explore in a real fibre.

Figure 11:
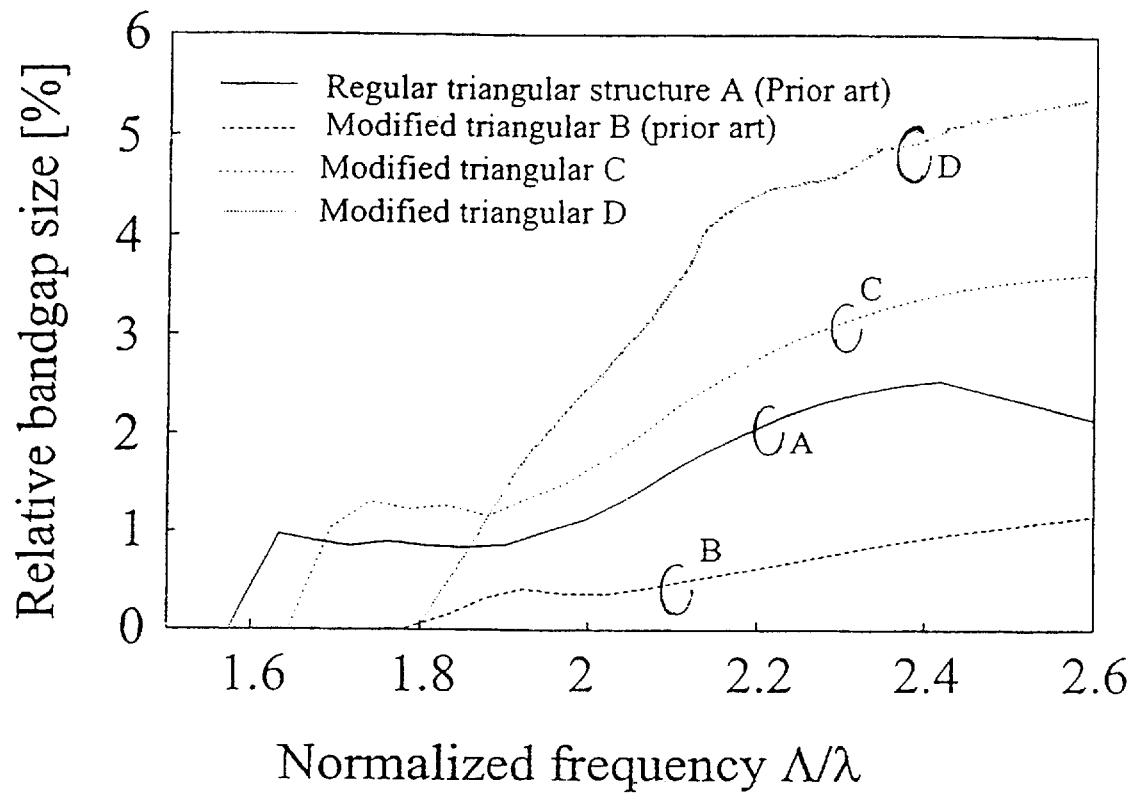
FIG. 11 illustrates the size of the bandgap which crosses the air line for the highest values of $\Lambda/\lambda$, i.e. the bandgap appearing for the largest structure dimensions for a fixed wavelength, as a function of normalised frequency. Four different structures are analysed, namely a regular triangular structure with an air filling fraction of 45% (Type A, see FIG. 10), a modified triangular structure (Type B, see FIG. 12) where small interstitial air voids have been introduced in a Honeycomb structure (this structure is known from the prior art of microstructured fibres), an optimised triangular structure where small interstitial air voids have been introduced in a Kagomé structure (Type C, see FIG. 13), and finally an optimised triangular structure (Type D), which is identical to the structure Type C, but with slightly larger interstitial air voids.
Figure 12:
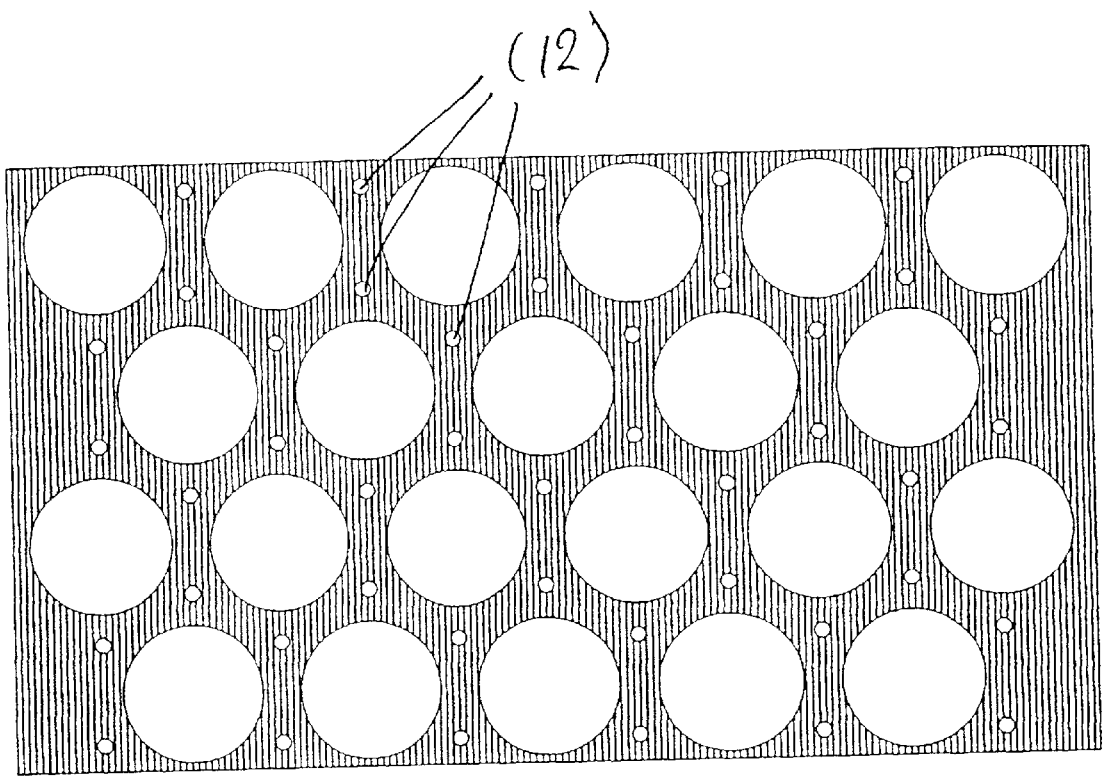
FIG. 12 shows a triangular structure with small interstitial voids placed mid between three adjacent, large voids. The interstitial voids form a Honeycomb structure.

FIG. 11 shows the relative size of the bandgap as a function of normalised frequency for the regular triangular structure of FIG. 10 (type A). The relative bandgap size is defined as the difference between the upper and lower frequencies of the bandgap divided by its centre frequency. In the figure three cases of modified triangular structures are also included where:

Type B is a regular triangular structure with additional small interstitial voids (12) introduced at mid position between three adjacent voids (their total filling fraction is 1%). This type of structure is schematically illustrated in FIG. 12, and is known from the prior art of photonic crystal fibres, as those small interstitial voids which have been found to remain at midpositions between three adjacent air voids. These interstitial voids have unintentionally been introduced in the cladding structure due to the fabrication technique involving close-packing of identical, circular capillary tubes. The interstitial voids form themselves a Honeycomb structure.

Figure 13:
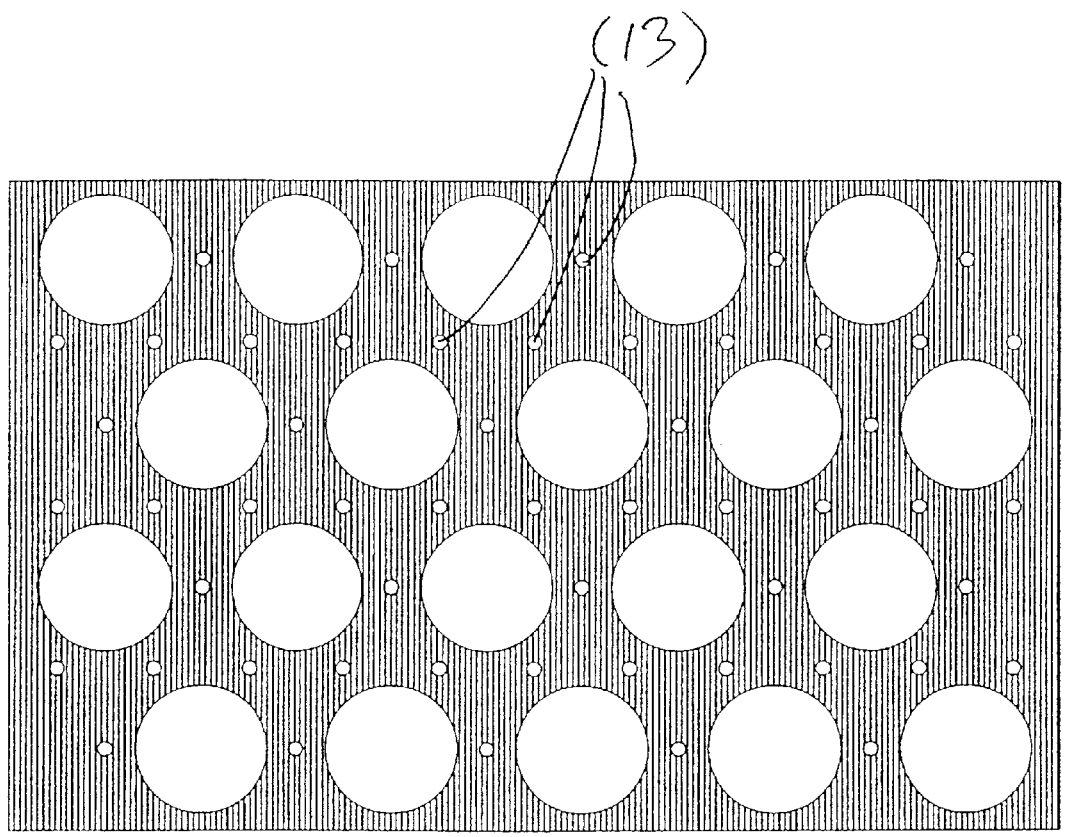
FIG. 13 shows a triangular structure with small interstitial voids placed mid between two adjacent, large voids. The interstitial voids form a Kagomé structure.

Type C is a regular triangular structure with additional small interstitial voids introduced at mid position between two adjacent voids (their total filling fraction is 1%). This type of structure is not known from the prior art and is covered by the present invention. The structure is schematically illustrated in FIG. 13. The interstitial voids (13) in this structure are arranged in a Kagomé structure.

Type D is the same structure as Type C, except that the total filling fraction of the interstitial voids is 5%.

For the basic structure (no interstitial voids) a maximum PBG size of approximately 2.5% at $\Lambda/\lambda$ around 2.4 is observed. This size is seen to decrease to about 1% by adding interstitial voids to the structure at the mid position between three adjacent voids. In contrast to this it is seen that by introducing almost similarly sized interstitial voids at mid position on the line connecting two adjacent voids the size of the bandgap is strongly increased. An even greater increase in PBG size (up to 5% at $\Lambda/\lambda$=2.4) may be achieved by increasing the size of the interstitial voids further at this position. It must further be emphasised that for a structure similar to Type B, but with interstitial voids with a total filling fraction of 5%, the bandgap was found to be completely closed.

Apart from the increase of the relative bandgap, it is of course very important to analyse the relative size of the bandgap at the values where it overlaps the air line (as this range is of importance for cladding structures in hollow core fibres). Such an analysis is presented in FIG. 14. Again the structures Type C and D are seen to be superior to the structures known from the prior art.

Figure 14:
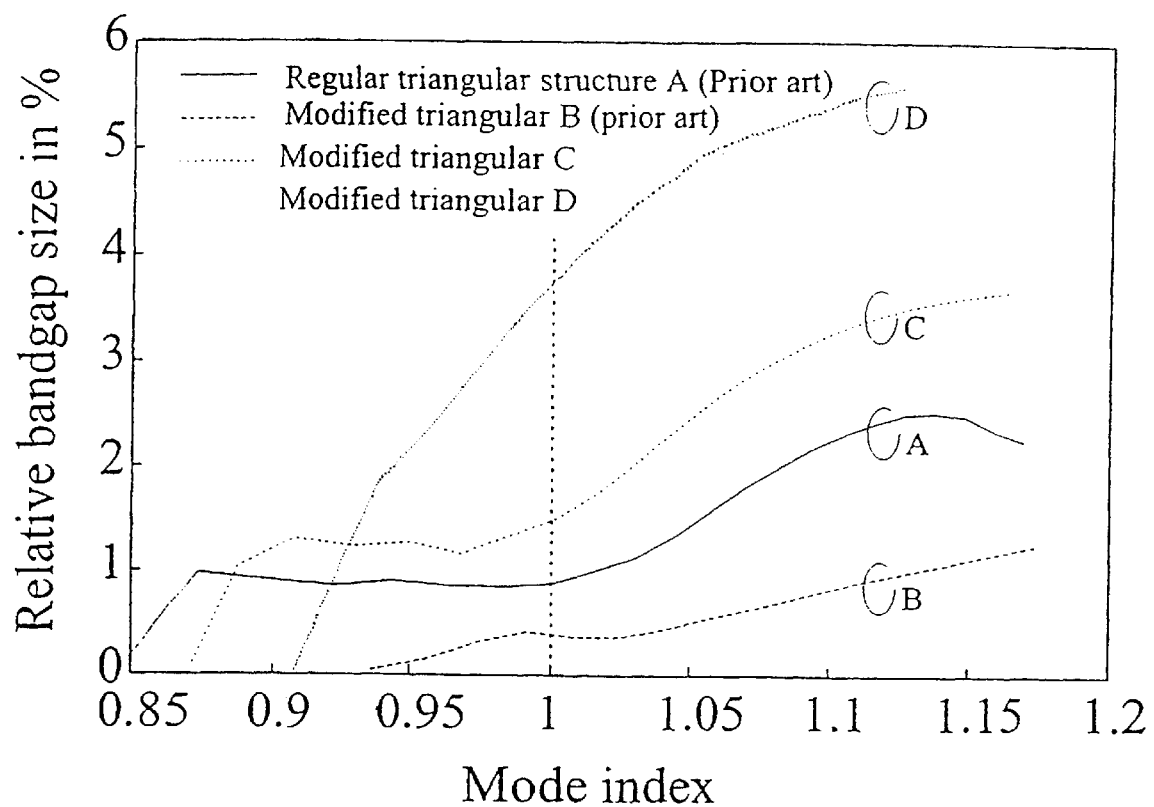
FIG. 14 illustrates the size of the bandgap as a function of the mode index (calculated using the center-frequency of the bandgap) for the four structures Type A, B, C and D.

In FIG. 14 the advantage of the optimised structures over the known structures is even more apparent than in FIG. 11. The optimised structure Type D is seen to increase the relative bandgap size by as much as four times compared to the basic triangular structure (to be compared at the mode index value equal to 1).

Although we have chosen to focus on the bandgap overlapping the air line for the highest $\Lambda/\lambda$-values, for completeness, it must be emphasised that a very strong suppression of all four bandgaps was found for the structure Type B (and furthermore only one narrow bandgap—not even crossing the air line—was found for a structure as Type B, but with interstitial voids having a filling fraction of 5%).

The above results illustrate how the concept of high-index nodes and veins are being used by the present inventors to design improved cladding structures. In short the design route states that in order to optimise photonic crystal structures with respect to obtaining wide bandgaps, the structures should have the most isolated nodes (high-index regions), and the nodes should contain the material parts with the highest refractive index. Finally, as those skilled in the art will recognise, the nodes should not be completely isolated (as the nodes would then act as individual high-index waveguides). This final requirement has two consequences, namely firstly, that the overall periodicity of the structure should be comparable to the free-space wavelength of the light, and secondly, that an upper limit for the void filling fraction do, in fact, exist. The first of these consequences puts yet another restrain on the dimensions of the structure (very small structures are required for operation in the visible and near-infrared). In contrast to this, the upper limit for the void filling fractions is irrelevant for all realistic fibres. The upper limit lies for voids with a diameter very close to the center-to-center void spacing, and voids of such sizes are practically impossible to realised for structures with the small dimensions required for the optical fibres. Therefore, in practise, to isolate the nodes as much as possible while retaining a large void filling fraction, provides the most optimised cladding structures for the fibres. As the veins may be either narrowed (and thereby isolate the nodes) in triangular photonic crystal structures if the center of additional (interstitial) voids fall approximately on the line connecting the centers of two adjacent primary voids, or the ability of the nodes to act as high-index centers may be degraded if the interstitial voids are positioned mid between three adjacent triangular voids, it is evident that interstitial voids may be either advantageous or disadvantageous depending on their location. It should again be emphasised how the interstitial voids which have been observed in photonic crystal fibres with a triangular void arrangement in the cladding, fall right in the centre of the nodes (thereby severely damaging their ability to act as high-index centres, and the cladding structure to exhibit PBG effect).

According to the outlined design route also cladding structures having the largest voids arranged in a Honeycomb or so-called Kagomé structure are advantageous. The advantages of Honeycomb structures have previously been documented (see Broeng et al., Optics Communications, Vol.156 (4–6), p. 240, November 1998). Both Honeycomb and Kagomé structures have intrinsically larger nodes and relatively narrower veins than the triangular structure. However, with respect to the second issue that must be addressed for the optimisation of the cladding structures for use in hollow core fibres, namely that the bandgaps must extend below the air, neither realistic Honeycomb nor Kagomé structures have been found to fulfill this necessary requirement. That no bandgaps have been found to extend below the air line for realistic Honeycomb and Kagomé structures are attributed to the fact that these structures have intrinsically lower void filling fractions than triangular structures with voids of similar sizes. The present inventors have therefore realised that triangular-like arrangements of voids form the best basis for cladding structures, which are optimised for use in hollow-core PBG fibres.

A further advantage of the already described new fabrication technique is that it does not only allow easy manufacturing of optical fibers with large void filling fractions, it allows as well flexible manufacturing of advanced structures, including the above-described improved cladding structures), and do thereby satisfy both requirements for realisation of PBG guiding optical fibers with a confinement of light in hollow cores.

Figure 15:
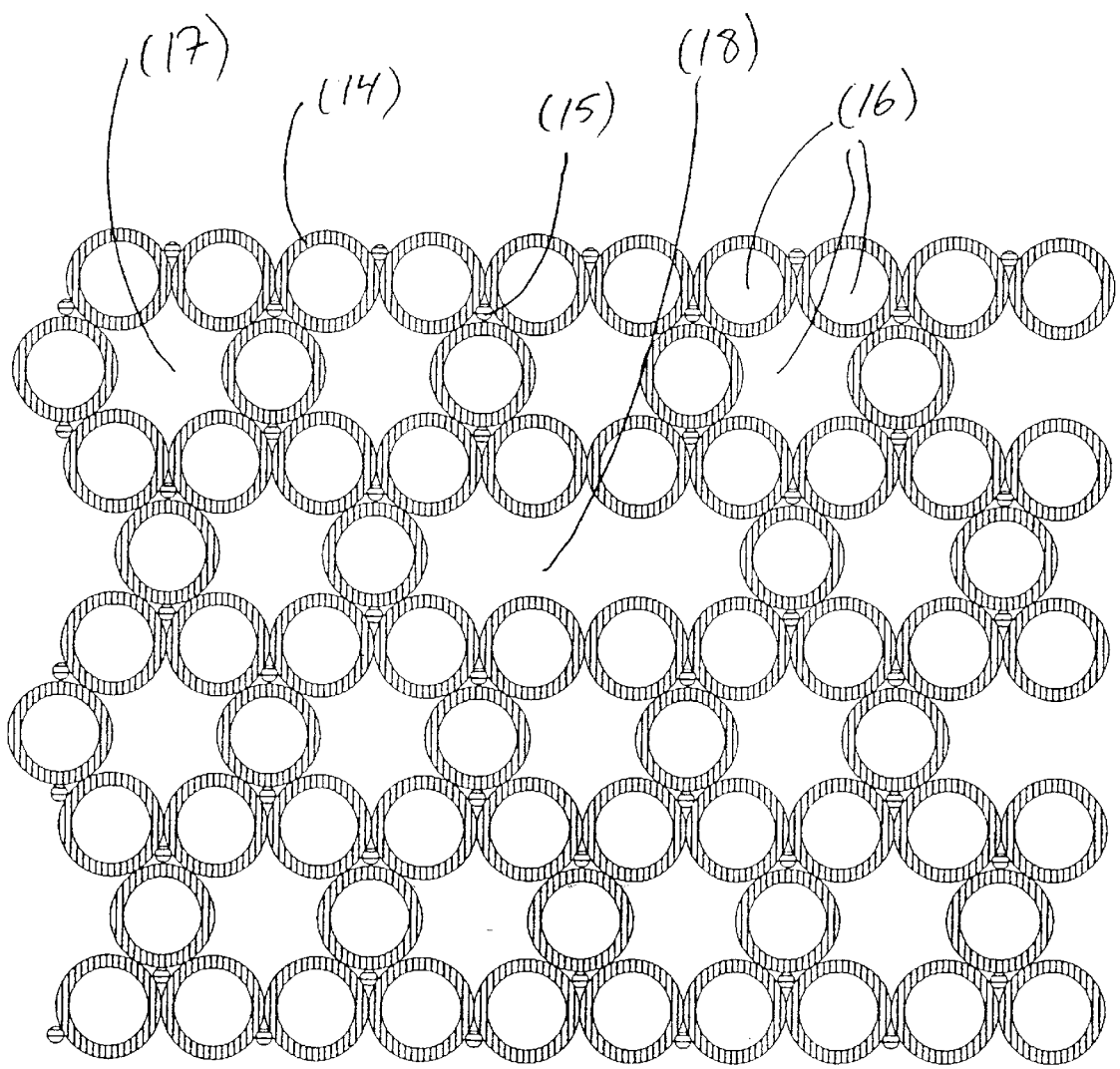
FIG. 15 schematically shows an embodiment of a preform cross-section. The preform is stacked using capillary tubes, rods and jigs. The cross-section presented in this figure is taken at a position where the jigs do not extend. The capillary tubes are arranged in a Kagomé structure. The rods have a smaller outer diameter than the capillary tubes, and they are placed at positions mid-between three capillary tubes. An asymmetric core region is easily introduced in the preform by omitting a single capillary tub e and two rods.

A preferred embodiment of an optimised cladding structure is illustrated in FIG. 15 (a cross-sectional view of the preform at a section not containing jigs is shown). The preform has a cladding structure, where the capillary tubes (14) are arranged in a Kagomé structure, and small solid rods (15) are positioned in a Honeycomb structure at positions corresponding to the nodes of the overall triangular structure (16) (formed from the capiliary-(14) and jig-introduced voids (17)). The figure further illustrates a preferred embodiment of an asymmetric core region (18) for the optimised fibre, which has been formed by breaking the periodic structure simply by leaving out a single capillary tube and two solid rods.

Figure 16:
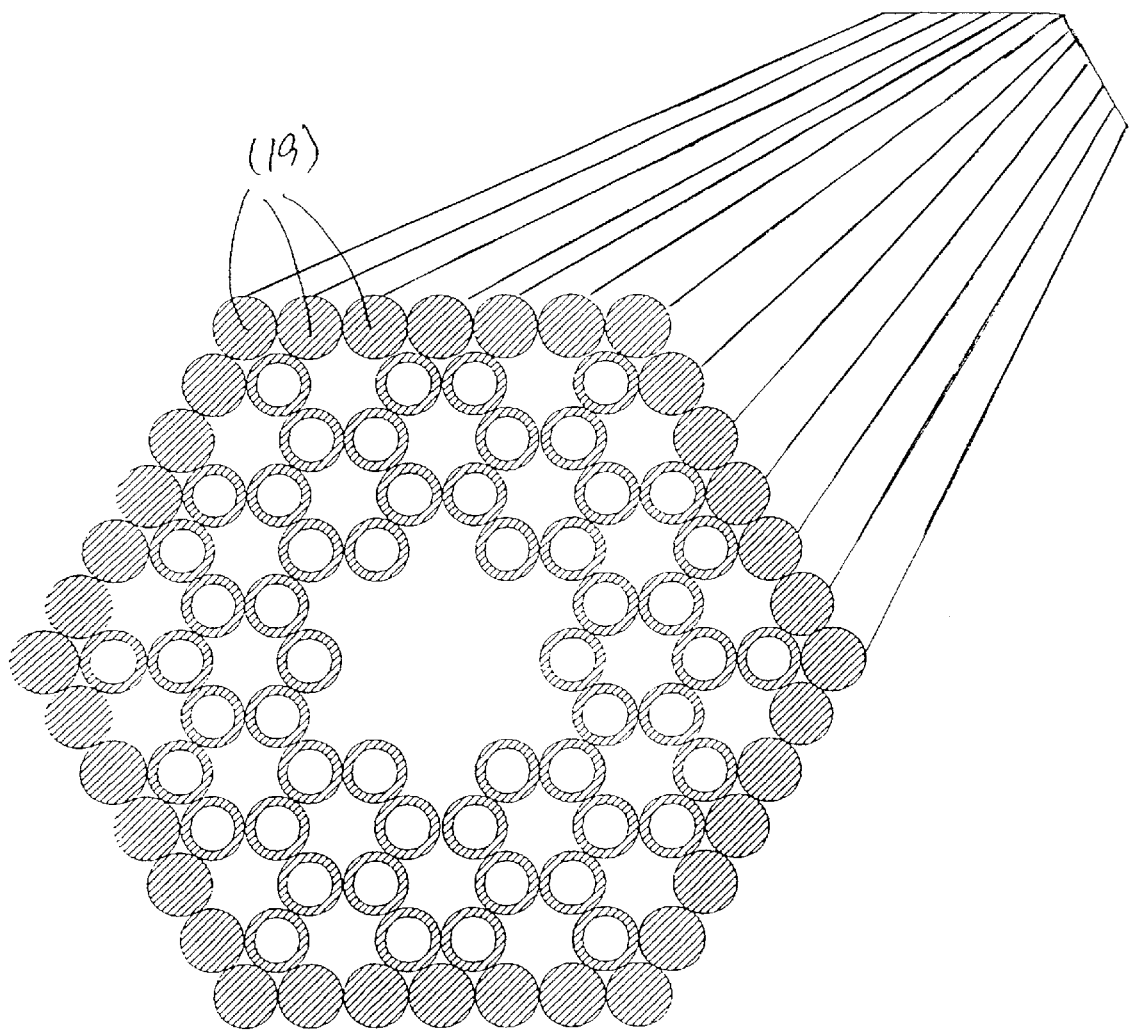
FIG. 16 schematically shows an example of a cross-section of a preform in which a large periodicity-breaking region has been introduced to form the core. The fibre core may easily be realised through the new fabrication technique, where in this specific case, an array of seven jigs are used to form the core region. A non-periodic structure is placed outside the inner cladding structure (which is required to be periodic in order for the cladding structure to exhibit photonic bandgap effects).

Another example of a fibre with a low-index core area has already been illustrated in FIG. 3. All cladding structures disclosed in this application may be combined with various realisations of the core area. Another example of a defect (or core) area covered by the present invention is illustrated in FIG. 16. Furthermore the figure illustrates an example of a periodic cladding structure, which at its outer interface is surrounded by a non-periodic structure. Since only a limited number of periods for the periodic structure are required to exhibit photonic bandgap effects, only the inner part of the cladding needs to be periodic. Therefore, as indicated in FIG. 16, the outer cladding need not be periodic. In this example a ring of rods (19) have been placed around the inner cladding (it should be noted that for a real fibre a minimum of two periods are expected to be required for the cladding structure to be able to exhibit sufficient photonic bandgap effects). A wide range of other outer cladding structures (which are not required to be periodic) may be thought of as well. The main function of the outer cladding structure is to provide robustness and stability to the final fibre. As the guided light is not influenced by this outer cladding, it may thus consist of many types of materials, i.e. homogenous silica. In particular it is possible to use conventional overcladding of the part of the preform that contains the periodicity.

The in case of optical fibres, this overcladding could further more improve the strength of the fibre so as to provide a fibre that is easier to splice and cleave. In a first aspect of the overcladded fibre, a circular outer fibre cross-section could be imagined, so that standard fibre fixtures may be used. However, also other overcladding tubes could be imagined, e.g., square or hexagonally shaped outer fibre cross-sections, which may be preferred in the case of highly polarisation preserving fibres, where the outer shape of the fibre could facilitate the localisation of fibre primary axes etc.

As an alternative to the conventional overcladding approach, the strong mode confinement of the PBG fibres could suggest another approach in which the fibre surrounding the core area is constructed by bundling capillary tubes and jigs into a closepacked arrangement according to the preferred design of the periodic cladding region. Outside of this periodic region, which have to be fixed in position, the outer fibre structure (corresponding to an outer cladding region) could be formed by packing of thinner glass rods, which could be mechanically shaken into place, because the key issue here not is to form a periodic structure. When the preform then later is drawn into a fibre, the outer cladding structure is melted together to form a (near) solid outer cladding. The only requirement for the outside placement of thin glass rods is that the surface tension due to an uneven distribution outside the periodic part of the fibre, do not result in a significant deformation of the periodicity.

Figure 17:
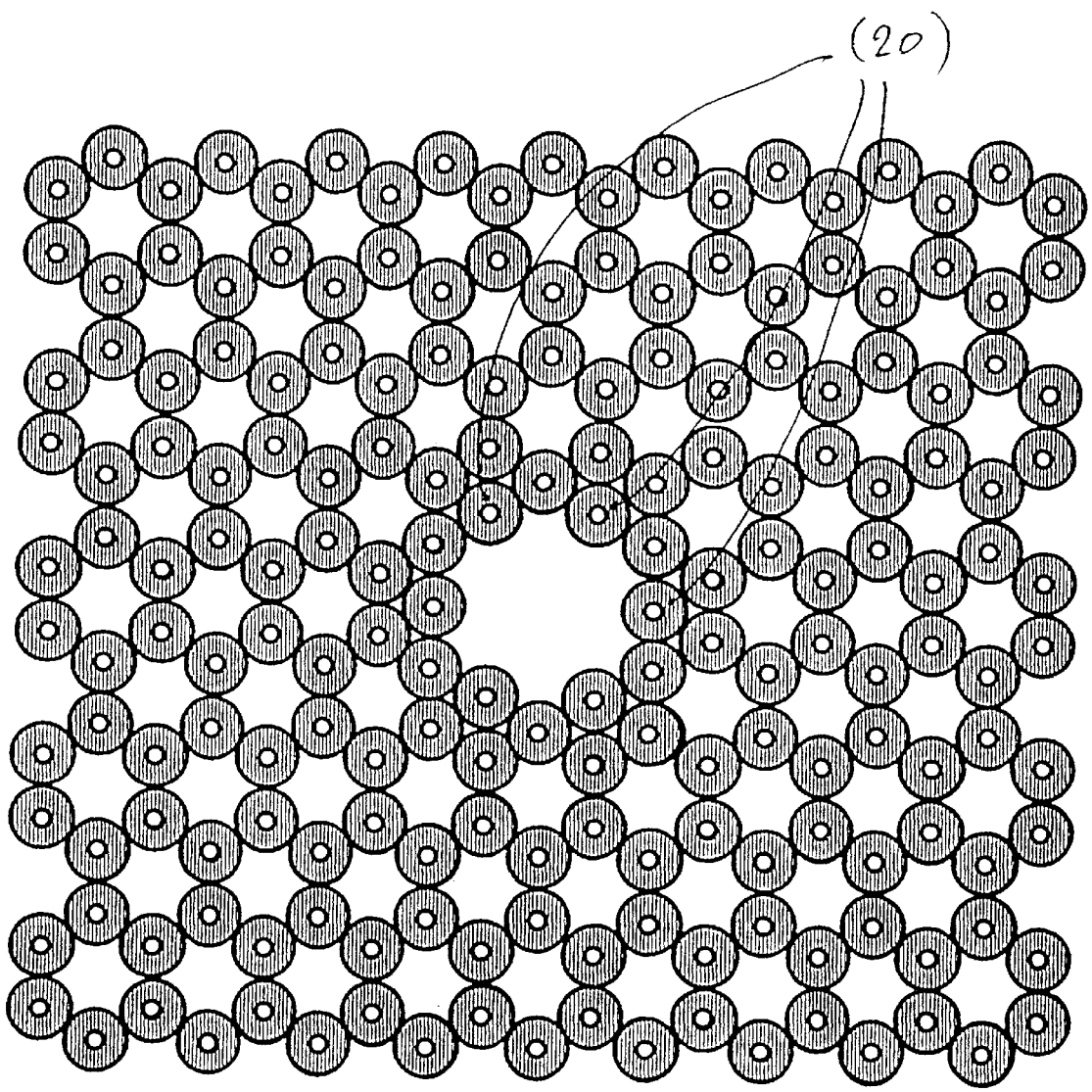
FIG. 17 shows a nearly circular core-forming void placed centrally in a cladding structure of Honeycomb-arranged capillary tubes. Extra capillary tubes have been introduced to "smoothen" the boundary between the core and cladding regions.

An example of the inner structure of a preform/fibre is shown in FIG. 17. In this example additional (non-periodic) capillary tubes (20) have be placed on the boundary between the core and cladding regions to provide a "smoothening" of the boundary surface. Such a "smoothening" may be of importance for reducing possible scattering losses, due to surface roughness.

Figure 18:
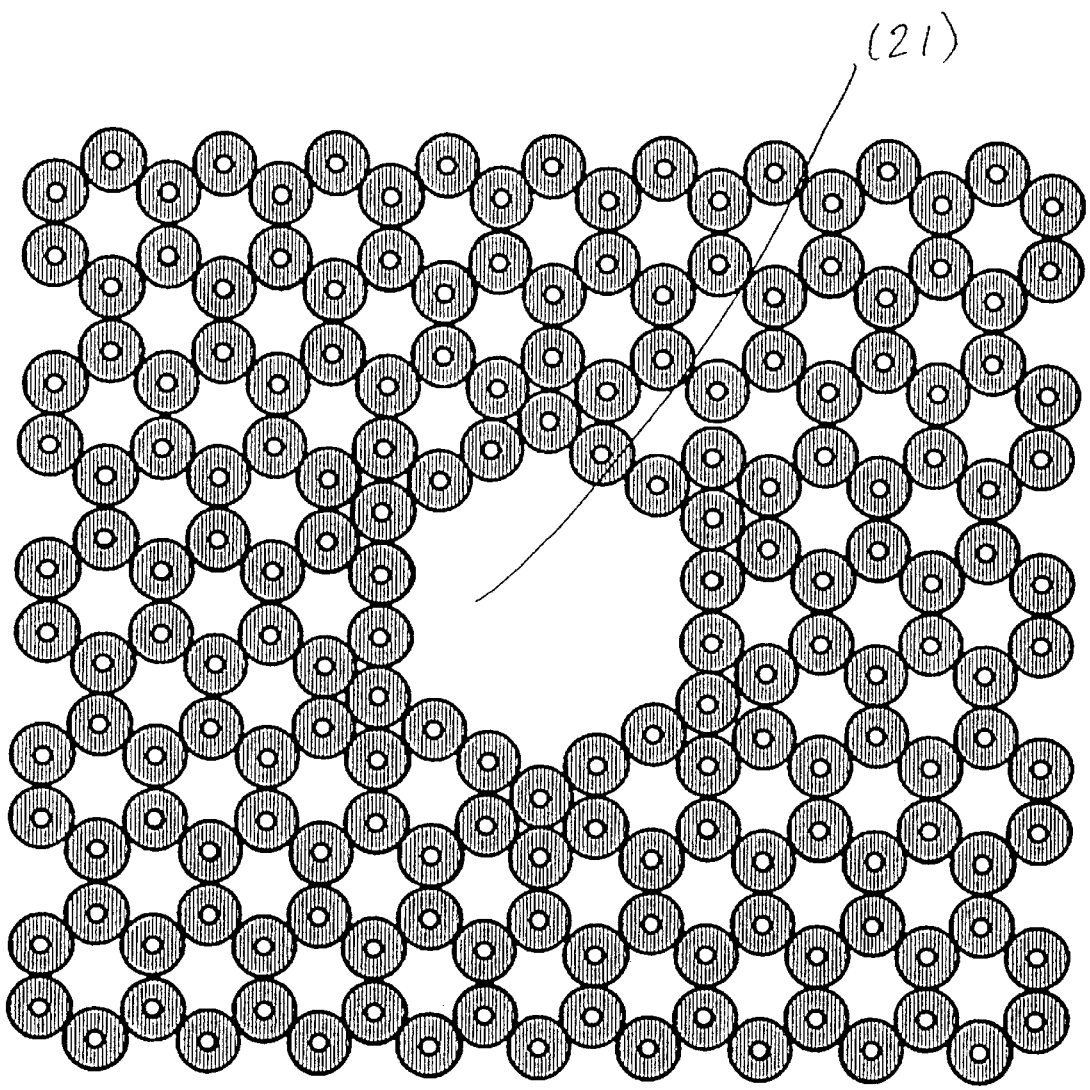
FIG. 18 shows an even larger, nearly circular core-forming void placed centrally in a cladding structure of Honeycomb-arranged capillary tubes. Again extra capillary tubes have been introduced to "smoothen" the boundary between the core and cladding regions.

Yet another example of a large "smoothened" core region (21) is illustrated in FIG. 18.

Figure 19:
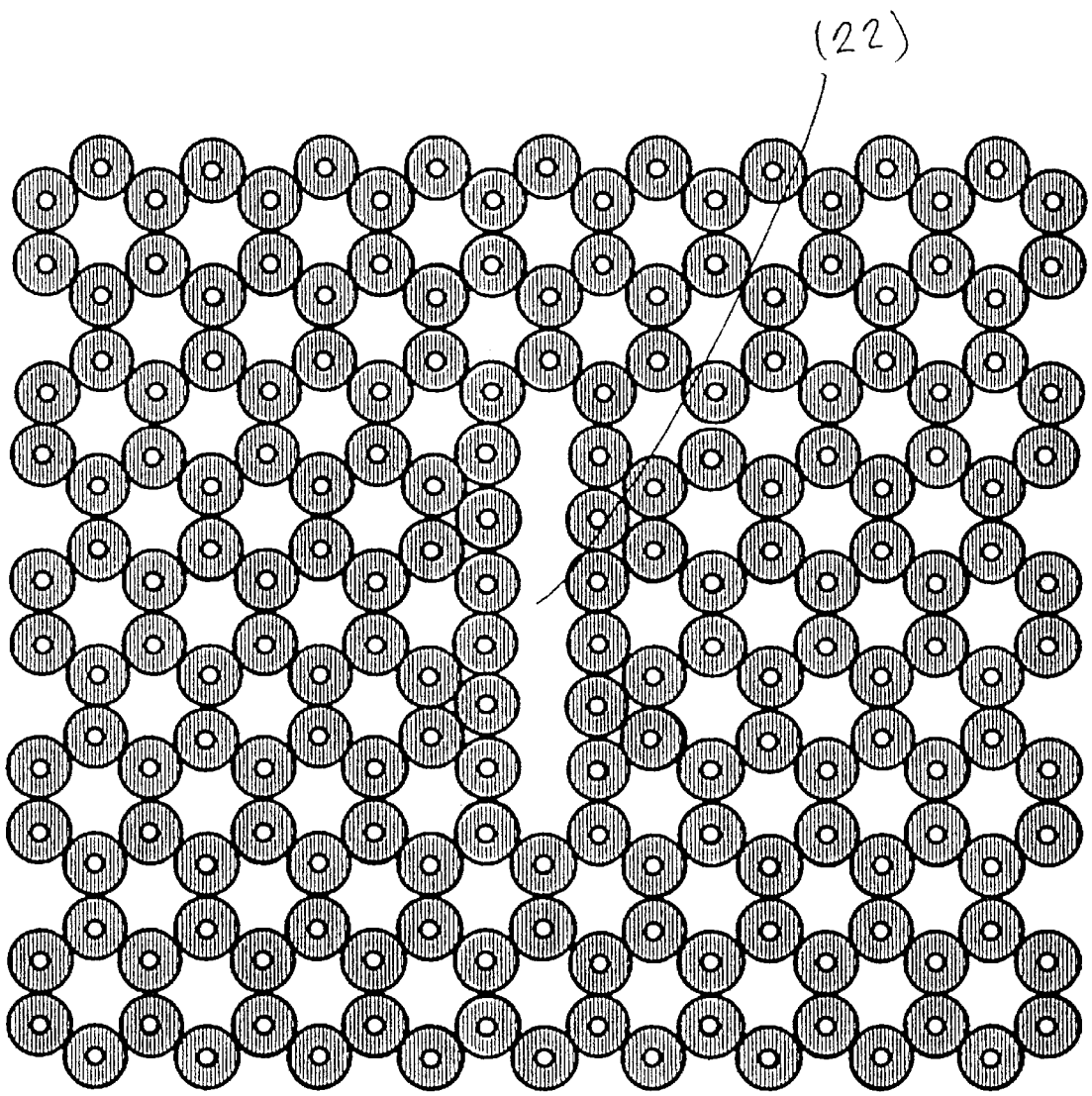
FIG. 19 illustrates an example in which a large, nearly rectangular core void is placed centrally in a cladding structure formed by circular, Honeycomb-arranged, capillary tubes. The cross-sectional area of the rectangular core is larger than the cross-sectional area of any of the individual voids of the cladding structure. Such non-circular core regions are important for the control of polarisation effects in the optical fibres.

Another important example of a large core region is illustrated in FIG. 19. The core (22) is strongly asymmetric, and such core designs will naturally be of high importance for controlling polarisation properties in bandgap guiding fibres.

Figure 20:
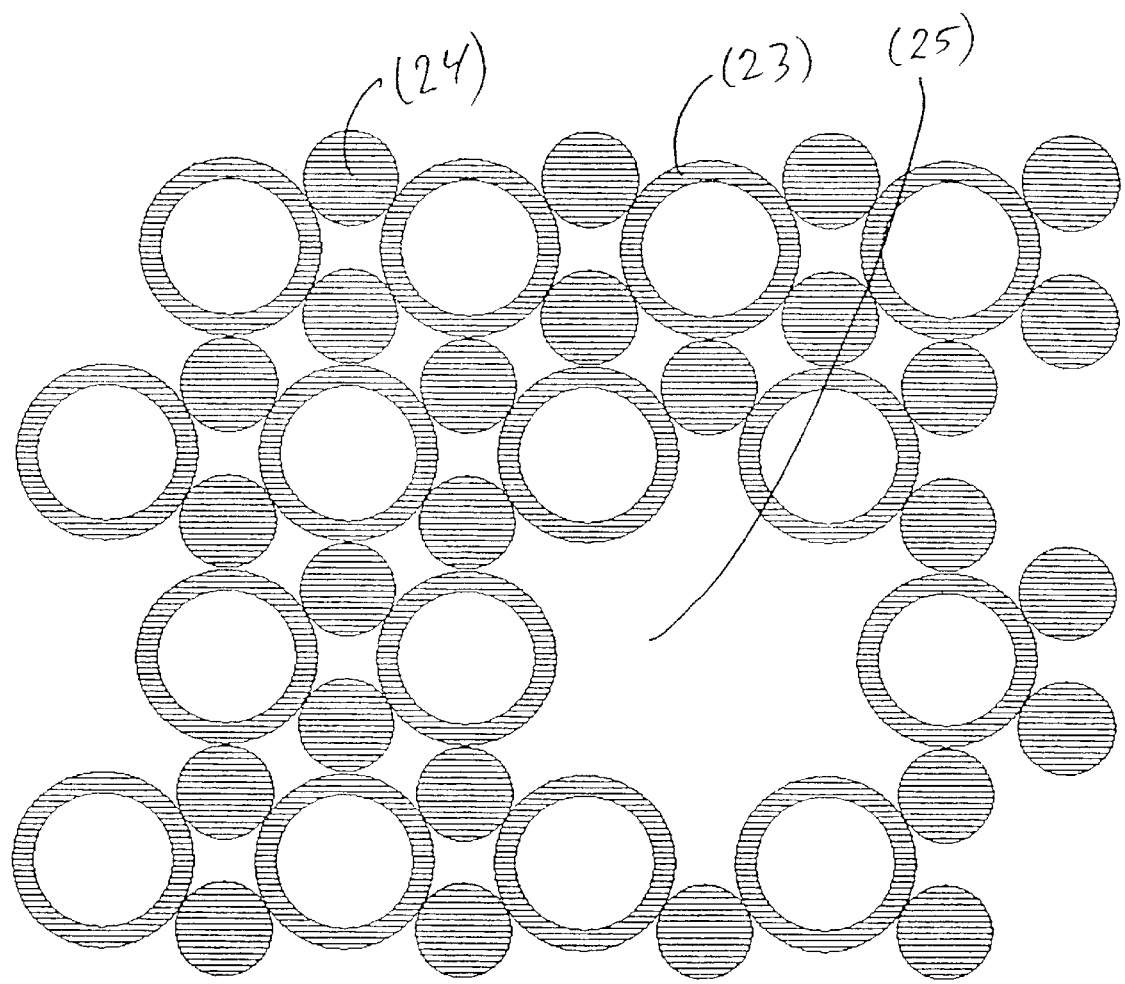
FIG. 20 shows an example of an advanced structure that may be realised using the new fabrication method.
Figure 21:
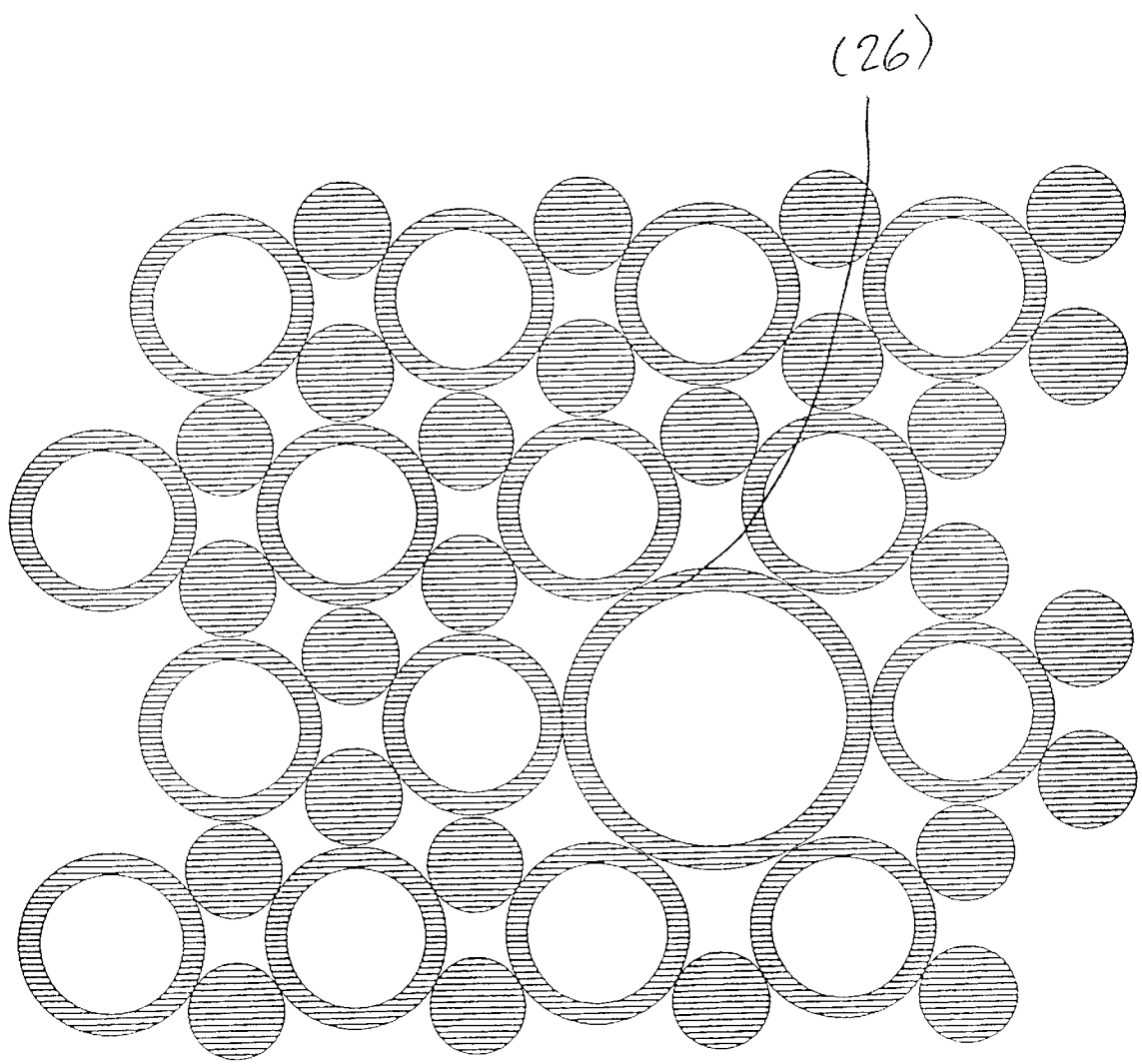
FIG. 21 shows another example of an advanced structure that may be realised using the new fabrication method. The structure is almost identical to FIG. 20, except that a single larger capillary tubes is forming the core.

Another example of the flexibility of the new fabrication method is illustrated in FIG. 20, where capillary tubes (23) of larger dimensions than the rods (24) are used to form a novel cladding structures. Jigs may be used for the fabrication of this structure to support the capillary tubes/rods as well as for realising the large core region (25). A smoothened core region for the design in FIG. 20 could also be realised by using a single even larger periodicity-breaking capillary tube to form the core. Such an example of an even larger capillary core tube (26) is illustrated in FIG. 21.

Figure 22:
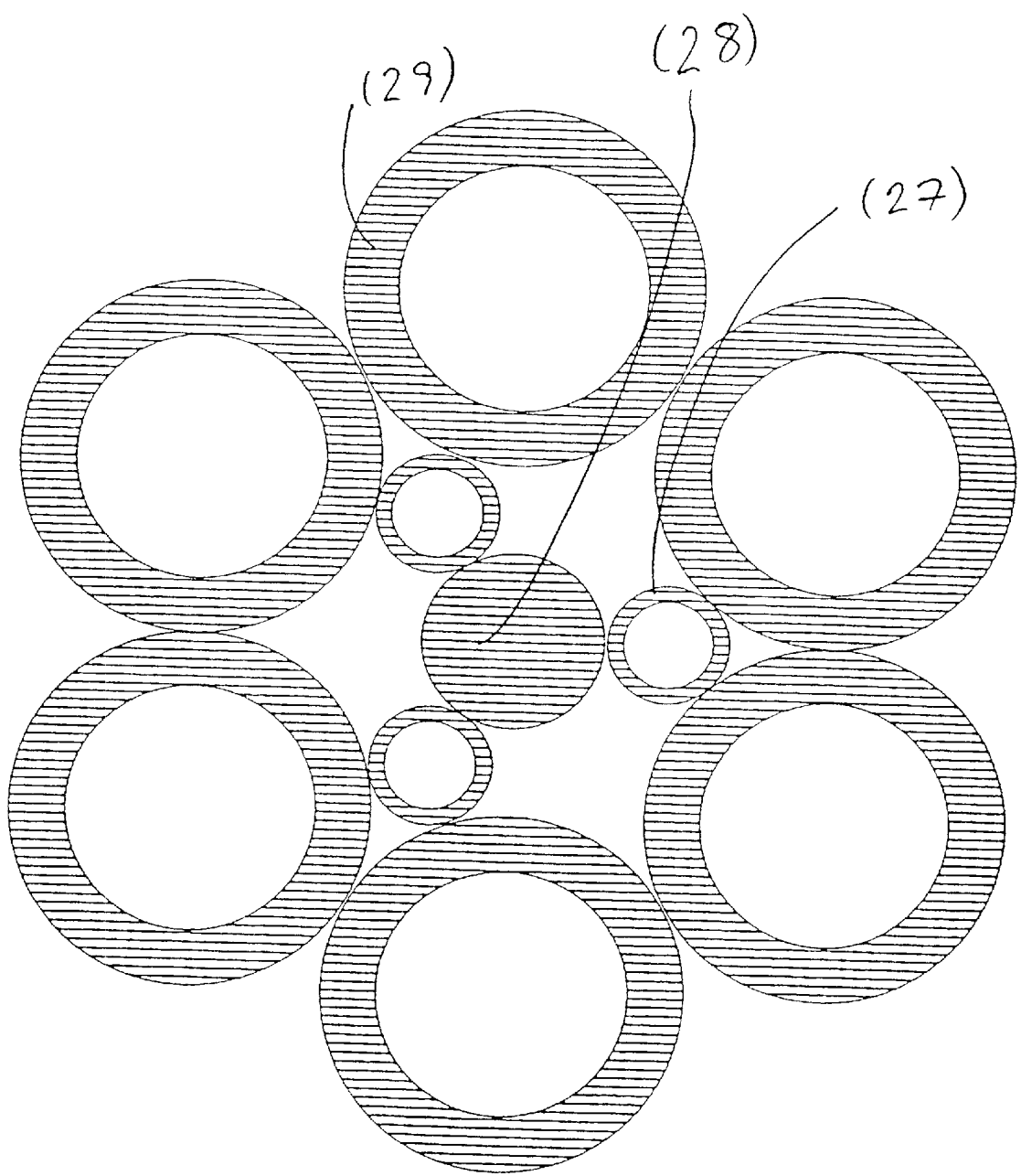
FIG. 22 shows an example of an advanced core structure that may be realised using the new fabrication method, where a combination of differently sized capillary tubes and rods are used.

Another example of an advanced structure, where capillary tubes of different sizes are used is illustrated in FIG. 22. Small capillary tubes (27) and rods (28) are used to support larger capillary tubes (29).

Although the structure of the final fibre resembles the structure of the preform, their structures are in general not identical. Its should, therefore, be pointed out that variations from the ideal structures described here may be introduced during fabrication, but as long as the fundamental physical limits of the fibres are preserved, the structures are covered by the present invention. It should, in particular, be noted that the examples of structures presented here not necessarily have to be formed by circular capillary tube-introduced voids, but any periodically repeated cross-sectional shape may be used to form the PBG's of the cladding as well as the core (e.g., voids of triangular, square, elliptical or any other shape may be applied).

Figure 23:
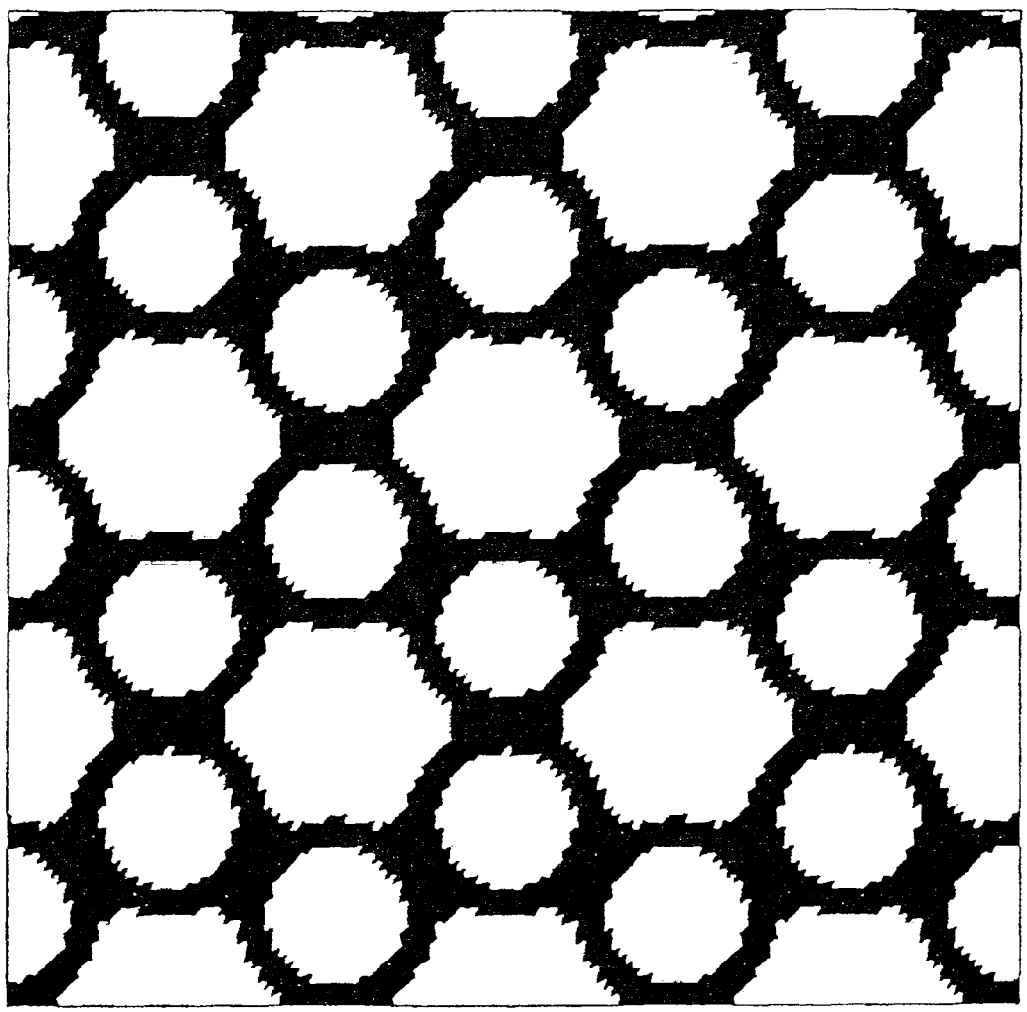
FIG. 23 schematically illustrates an example of a periodic cladding structure, as it may appear in the final fibre. The boundaries between the voids and the background should be smooth, but appear rough in the figure due to the numerical simulation of the structure.

An example of a final structure, as it may appear using the new fabrication process, is schematically illustrated in FIG. 23. It should be noted that the numerical accuracy for the simulation of the final structure was limited, resulting in a limited resolution of the illustration in FIG. 23. The interfaces between the voids and the background material do, therefore, not appear smooth as they would in a real fibre.

Figure 24:
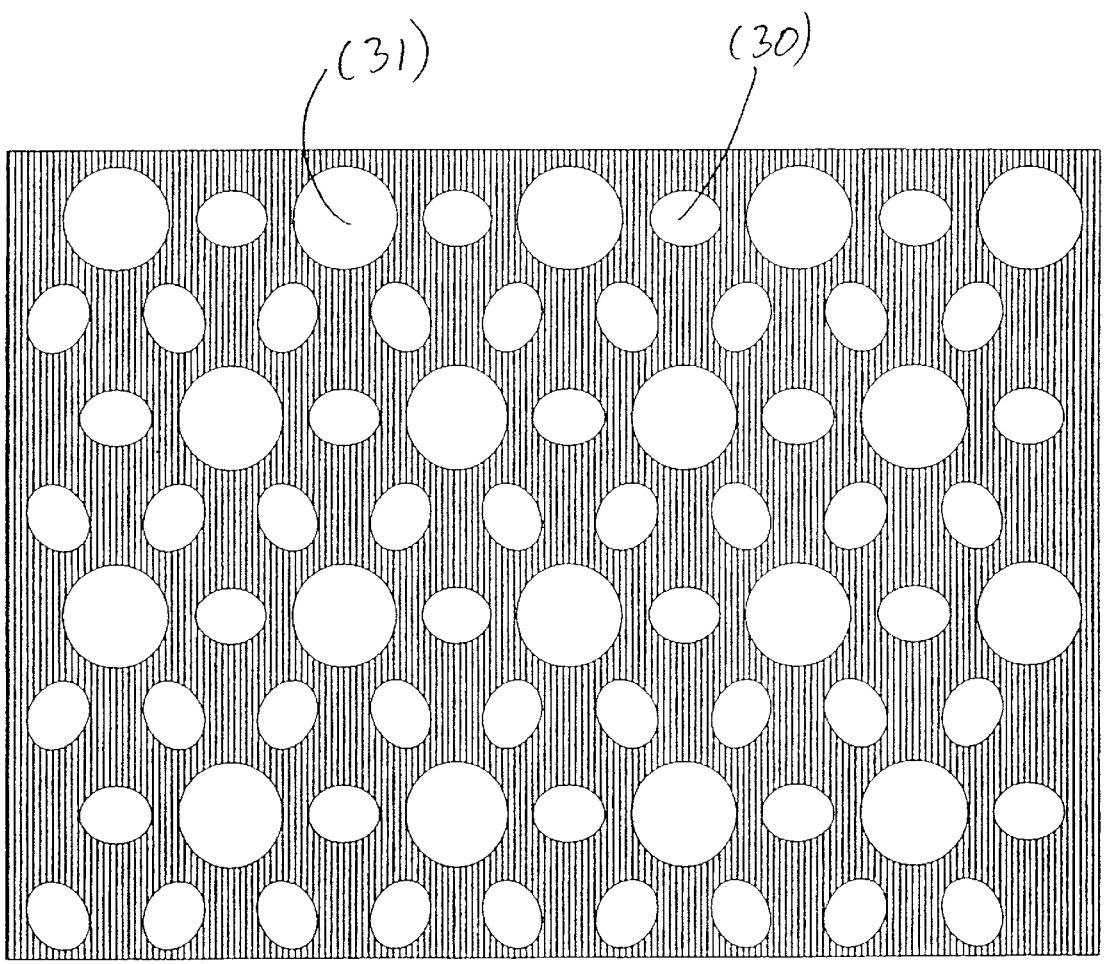
FIG. 24 schematically illustrates an example of a periodic cladding structure, as it may appear in the final fibre.

Another example of a final structure is illustrated in FIG. 24, where the initially circular capillary-introduced voids (30) have obtain a non-circular shape, and the jig-introduced voids have become nearly-circular (31).

Figure 25:
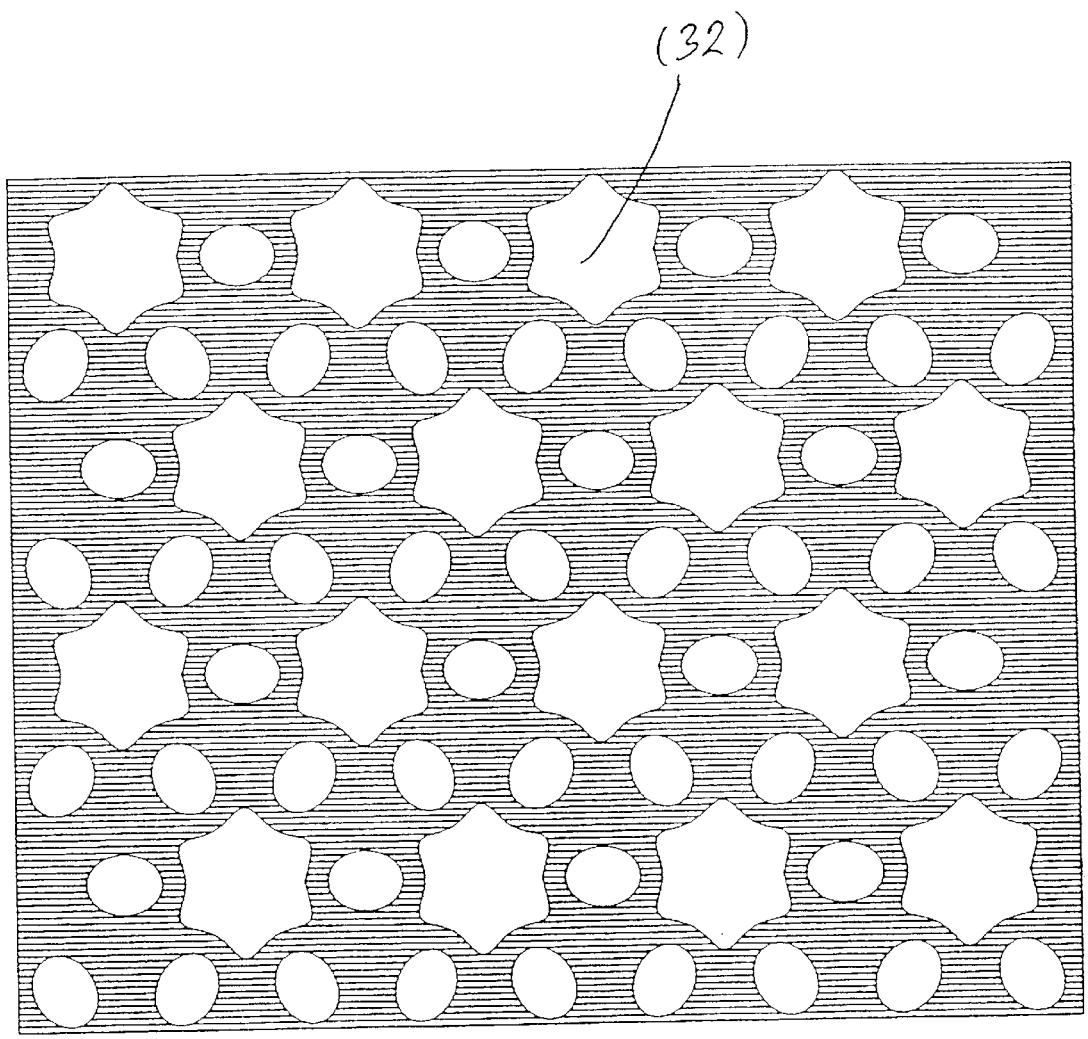
FIG. 25 schematically illustrates another example of a periodic cladding structure, as it may appear in the final fibre.

Yet another example of a final structure is illustrated in FIG. 25, where the jig-introduced voids (32) have been smoothened.

Figure 26:
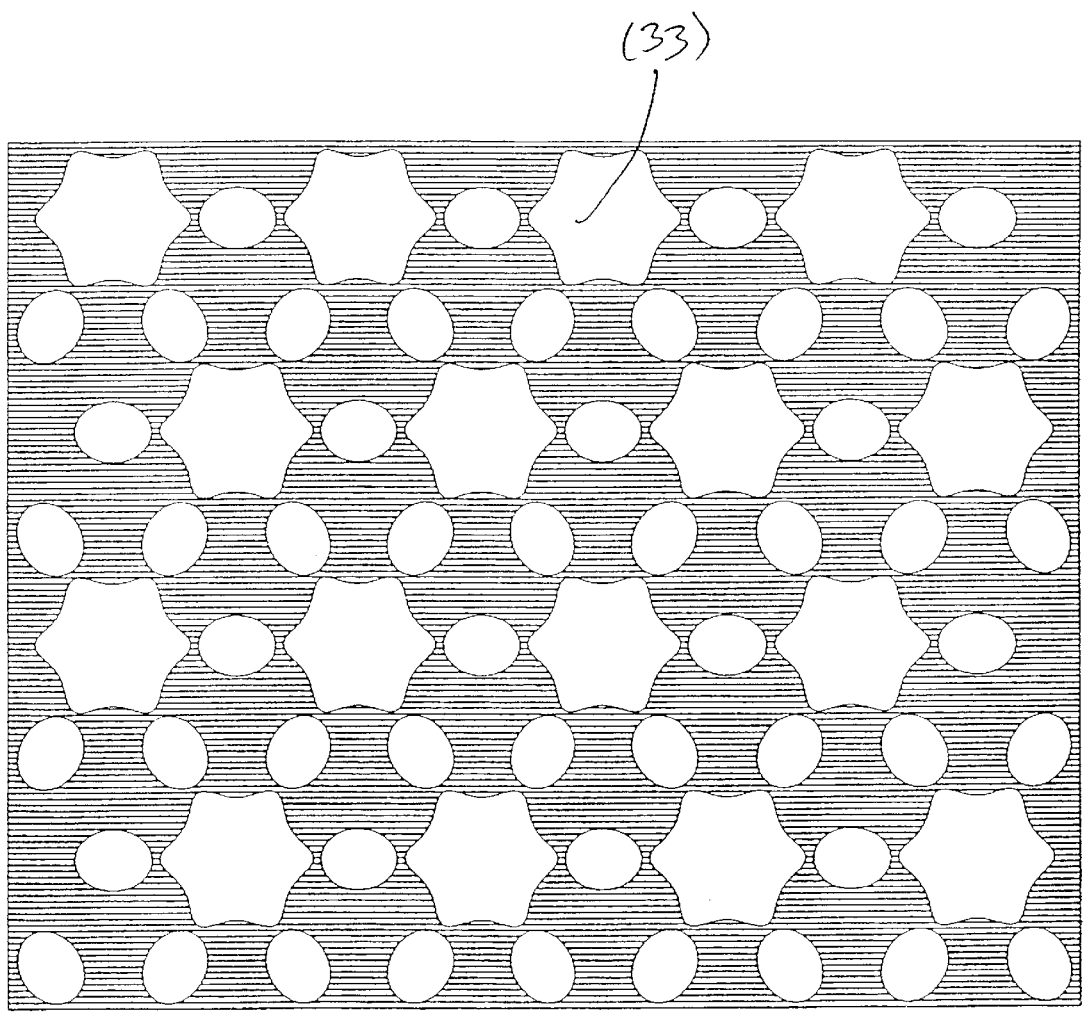
FIG. 26 schematically illustrates another example of a periodic cladding structure, as it may appear in the final fibre.

As the new fabrication method has a flexibility which allows e.g. very small rods to be placed at the corner-edges of the voids, a final structure as illustrated in FIG. 26 is also feasible. Compared to FIG. 25, the jig-introduced voids (33) appear to be rotated by an angle of 30°.

Finally for the discussion of the cladding structures it must be noted that all the here disclosed cladding structures may be adapted to multi-core fibre configurations.

Figure 27:
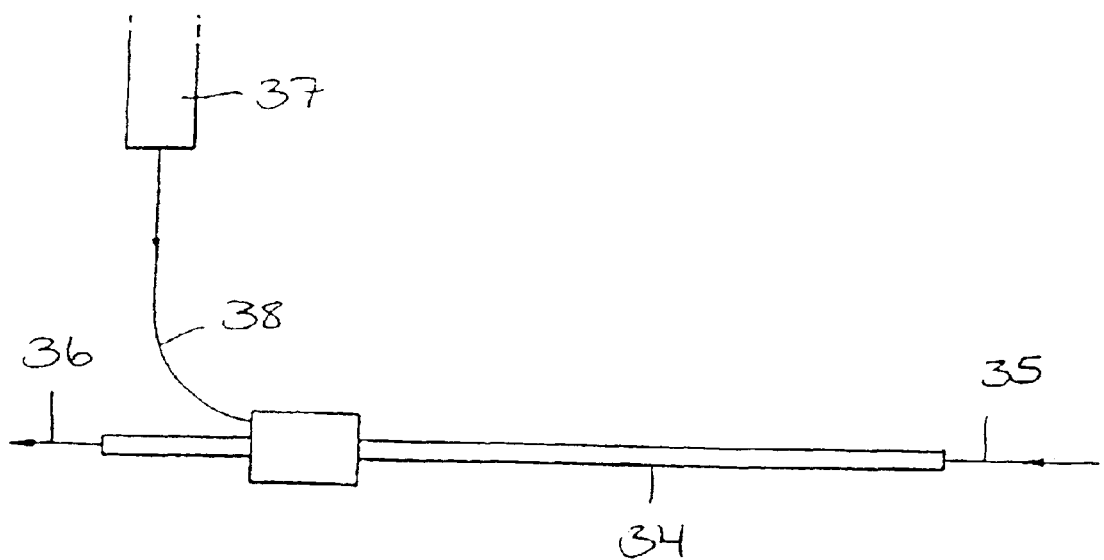
FIG. 27 shows a fibre amplifier for amplifying an optical signal using a length of the optical fibre according to the invention.

Apart from the passive guidance of light, the here disclosed cladding structures and fibres may be used in various applications. FIG. 27 shows an example of a fibre amplifier comprising a length of the fibre according to the invention (34), an input signal which is to be amplified (35), an output signal which has been amplified (36) and a source of radiation (37) for providing a pump signal (38). The pump signal typically pumps a dopant which has been introduced into the length of fibre.

Figure 28:
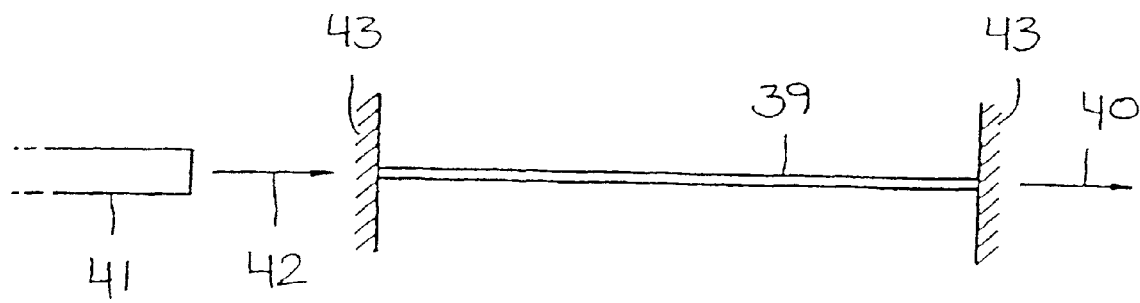
FIG. 28 shows a fibre laser for outputting an optical signal using a length of the optical fibre according to the invention.

In FIG. 28 shows an example of a fibre laser for providing laser radiation comprising a length of the fibre according to the invention (39), an output signal (40), and a source of radiation (41) for providing a pump signal (42). The fibre laser further comprises means for reflecting (43) the signal travelling inside the laser cavity.

PCF's with new functionalities may be fabricated by introducing regions within the fibres with special doping materials, or even materials that deviates significantly from the fibre basis material (e.g., glass, or polymers). These additional materials could for instance be rare-earth dopants, specially ultra-violet (UV) sensitive materials, or even semiconductors or metals.

The fabrication process may comprise the introduction of thin rods of doped (or different) material at well-defined locations in the closely packed, periodic basis material structure. Alternatively, some of the capillary tubes could be made from a doped material, or the preform (or parts of it) could even be placed in solutions of materials that could diffuse or bind to the basis material rods and tubes. Since specific parts of the preform could be treated individually before further stacking or alternative processing would continue, this approach allows for a very high degree of flexibility.

What is claimed is:

1. An optical fibre with a waveguide structure having a longitudinal direction, said optical fibre comprising:
    a core region extending along the longitudinal direction,
    a cladding region extending along the longitudinal direction, said cladding region comprising an at least substantially two-dimensionally periodic structure comprising elongated elements each having a centre axis extending in the longitudinal direction of the waveguide, the elongated elements having a refractive index being lower than a refractive index of any material adjacent to the elongated elements,
    the periodic structure being, in a cross-section perpendicular to the longitudinal direction, defined by at least one unit cell, wherein, for each unit cell:
    any distance between centre axes of two neighbouring elongated elements does not exceed 2 $\mu$m, and
    the sum of all areas of all elements, which areas are comprised within a given unit cell, is larger than 0.15 times the area of that unit cell.

2. An optical fibre according to claim 1, wherein any distance between centre axes of two neighbouring elongated elements is smaller than 1.9 $\mu$m, smaller than 1.8 $\mu$m, smaller than 1.6 $\mu$m, smaller than 1.4 $\mu$m, smaller than 1.2 $\mu$m, smaller than 1.0 $\mu$m, smaller than 0.8 $\mu$m, or smaller than 0.6 $\mu$m.

3. An optical fibre according to claim 1, wherein, for a given unit cell, the sum of all areas of all elements within the unit cell is larger than a constant times the area of that unit cell, said constant being larger than 0.2, larger than 0.25, larger than 0.3, larger than 0.4, larger than 0.5, larger than 0.6, larger than 0.7, or larger than 0.8.

4. An optical fibre according to claim 1, wherein for each unit cell:
    a first circle is defined as the largest circular area possible having a centre not positioned outside the unit cell and not enclosing any part of any elongated elements, and wherein
    the centres of those elongated elements, parts of which are within a distance of 1.5 or less, 1.2 or less, 1.1 or less times the radius of the first circle from the centre of the first circle, define the vertices of a polygon with three or more sides.

5. An optical fibre according to claim 4, wherein the polygon is a regular polygon.

6. An optical fibre according to claim 4, wherein the polygon is a triangular, rectangular, quadratic, or hexagonal polygon.

7. An optical fibre according to claim 1 further comprising further, elongated elements each having a centre axis extending in the longitudinal direction of the waveguide, the further, elongated elements having a refractive index being higher than a refractive index of any material adjacent to the secondary, elongated elements, and each having a centre not positioned outside the unit cell, and each having an area not exceeding the area of the unit cell.

8. An optical fibre according to claim 7, wherein at least part of the further, elongated elements, in the cross-section, define a triangular structure, a Honeycomb structure, or a Kagomé structure.

9. An optical fibre according to claim 8, wherein the further, elongated elements, in the cross-section, are at least partly comprised within the first circle.

10. An optical fibre according to claim 9, wherein the centres of at least part of the further, elongated elements, in the cross section, substantially coincide with the centre of the first circle.

11. An optical fibre with a waveguide structure having a longitudinal direction, said optical fibre comprising:
    a core region extending along the longitudinal direction,
    a cladding region extending along the longitudinal direction, said cladding region comprising an at least substantially two-dimensionally periodic structure comprising:
    primary, elongated elements each having a centre axis extending in the longitudinal direction of the waveguide, the primary elements having a refractive index being lower than a refractive index of any material adjacent to the primary elements,
    secondary, elongated elements each having a centre axis extending in the longitudinal direction of the waveguide, the secondary elements having a refractive index being lower than a refractive index of any material adjacent to the secondary elements,
    wherein any area of any primary element is larger than any area of any secondary element, and wherein
    the periodic structure being, in a cross-section perpendicular to the longitudinal direction, defined by at least one unit cell, wherein, for each unit cell:
    the sum of the areas of secondary elements, which areas are comprised within a given unit cell, is larger than 0.09 times the area of that unit cell.

12. An optical fibre according to claim 11, wherein any area of any primary element is larger than a constant times any area of any secondary element, said constant being larger than 1.1, larger than 1.2, larger than 1.3, as larger than 1.4, larger than 1.5, larger than 2, larger than 5, larger than 10, larger than 15, larger than 20, or larger than 50.

13. An optical fibre according to claim 11, wherein, for a given unit cell, the sum of all areas of the secondary elements within the unit cell is larger than 0.1, larger than 0.15, larger than 0.2, larger than 0.25, larger than 0.3, larger than 0.4, larger than 0.5, or larger than 0.6.

14. An optical fibre according to claim 11, wherein for each unit cell:
a first circle is defined as the largest circular area possible having a centre not positioned outside the unit cell and not enclosing any part of any primary, elongated elements, and wherein
the centres of those primary, elongated elements, parts of which are within a distance of 1.5 or less, 1.2 or less, or 1.1 or less times the radius of the first circle from the centre of the first circle, define the vertices of a first polygon with three or more sides.

15. An optical fibre according to claim 14, wherein the first polygon is a regular triangular polygon.

16. An optical fibre according to claim 11, wherein at least part of the primary, elongated elements, in the cross section, define a triangular structure.

17. An optical fibre according to claim 14, wherein none of the centres of the secondary, elongated elements, in the cross section, coincide with the centre of the first circle.

18. An optical fibre according to claim 11, wherein the centres of at least part of the secondary, elongated elements, in the cross section, are positioned substantially along a line connecting the centres of two adjacent primary, elongated elements.

19. An optical fibre according to claim 11 further comprising further, elongated elements
each having a centre axis extending in the longitudinal direction of the waveguide, the further, elongated elements having a refractive index being higher than a refractive index of any material adjacent to the further, elongated elements, and each having a centre not positioned outside the unit cell, and each having an area not exceeding the area of the unit cell.

20. An optical fibre according to claim 19, wherein at least part of the further, elongated elements, in the cross-section, define a triangular structure, a Honeycomb structure, or a Kagomé structure.

21. An optical fibre according to claim 11 or 19 wherein the further, elongated elements, in the cross-section, are at least partly comprised within the first circle.

22. An optical fibre according to claim 21, wherein the centres of at least part of the further, elongated elements, in the cross section, substantially coincide with the centre of the first circle.

23. An optical fibre according to claim 11 or 19, wherein, for a given unit cell, the sum of all areas of primary elements within the unit cell is larger than a constant times the area of that unit cell, said constant being larger than 0.1, larger than 0.15, larger than 0.2, larger than 0.25, larger than 0.3, larger than 0.4, larger than 0.5, larger than 0.6, larger than 0.7, or larger than 0.8.

24. An optical fibre with a waveguide structure having a longitudinal direction, said optical fibre comprising:
a core region extending along the longitudinal direction,
a cladding region extending along the longitudinal direction, said cladding region comprising an at least substantially two-dimensionally periodic structure comprising:
primary, elongated elements each having a centre axis extending in the longitudinal direction of the waveguide, the primary elements having a refractive index being lower than a refractive index of any material adjacent to the primary elements,
secondary, elongated elements each having a centre axis extending in the longitudinal direction of the waveguide, the secondary elements having a refractive index being lower than a refractive index of any material adjacent to the primary elements,
wherein any area of any primary element is larger than any area of any secondary element, and wherein, in a cross section perpendicular to the longitudinal direction the primary, elongated elements define a triangular structure,
wherein the periodic structure being, in the cross-section, defined by at least one unit cell, wherein, for each unit cell:
a first circle is defined as the largest circular area possible having a centre not positioned outside the unit cell and not enclosing any part of any primary, elongated elements, and wherein
the centres of any of the secondary, elongated elements, in the cross section, do not coincide with the centre of the first circle.

25. An optical fibre according to claim 24, wherein any area of any primary element is larger than a constant times any area of any secondary element, said constant being larger than 1.1, larger than 1.2, larger than 1.3, larger than 1.4, larger than 1.5, larger than 2, larger than 5, larger than 10, larger than 20, larger than 50, larger than 100, larger than 200, or larger than 500.

26. An optical fibre according to claim 24, wherein for each unit cell:
the sum of all areas of the secondary elements within the unit cell is larger than 0.005 times the area of that unit cell, larger than 0.01, larger than 0.05, larger than 0.1, larger than 0.15, larger than 0.2, larger than 0.25, larger than 0.3, larger than 0.4, or larger than 0.5 times the area of that unit cell.

27. An optical fibre according to claim 24, wherein at least part of the secondary, elongated elements, in the cross-section, define a triangular structure, a Honeycomb structure, or a Kagomé structure.

28. An optical fibre according to claim 24, wherein at least part of the secondary, elongated elements, in the cross section, have their centres positioned substantially along a line connecting the centres of two adjacent primary, elongated elements.

29. An optical fibre according to claim 24 further comprising further, elongated elements
each having a centre axis extending in the longitudinal direction of the waveguide, the further, elongated elements having a refractive index being higher than a refractive index of any material adjacent to the further, elongated elements, and each having a centre not positioned outside the unit cell, and each having an area not exceeding the area of the unit cell.

30. An optical fibre according to claim 29, wherein at least part of the further, elongated elements, in the cross-section, define a triangular structure, a Honeycomb structure, or a Kagomé structure.

31. An optical fibre according to claim 29, wherein the further, elongated elements, in the cross-section, are at least partly comprised within the first circle.

32. An optical fibre according to claim 31, wherein the centres of at least part of the further, elongated elements, in the cross section, substantially coincide with the centre of the first circle.

33. An optical fibre according to claim 24 or 29, wherein, for a given unit cell, the sum of all areas of primary elements within the unit cell is larger than a constant times the area of that unit cell, said constant being larger than 0.1, larger than 0.15, larger than 0.2, larger than 0.25, larger than 0.3, larger than 0.4, larger than 0.5, larger than 0.6, larger than 0.7, or larger than 0.8.

34. An optical fibre according to claim 1, 11, or 24 where the material adjacent to the elongated elements have a refractive index larger than 1.0, larger than 1.2, larger than 1.3, larger than 1.4, larger than 1.45, larger than 1.5, larger than 1.75, larger than 2.0, larger than 2.5, larger than 3.0, larger than 3.5, or larger than 4.0.

35. An optical fibre according to the preceding claim 1, 11, or 24 where the material adjacent to the elongated elements comprise silica-based materials.

36. An optical fibre according to claim 1, 11, or 24 where the material adjacent to the elongated elements comprise polymer-based materials.

37. An optical fibre according to claim 1, 11, or 24 where those elongated elements having a refractive index being lower than a refractive index of any material adjacent to the elongated element have a refractive index equal to 1.

38. An optical fibre according to claim 1, 11, or 24 where at least part of those elongated elements having a refractive index being lower than a refractive index of any material adjacent to the elongated element comprise a vacuum, a liquid or a gas.

39. An optical fibre according to the preceding claim 7, 19, or 29 where those elongated elements having a refractive index being higher than a refractive index of any material adjacent to the elongated element have a refractive index larger than 1.3, larger than 1.4, larger than 1.45, larger than 1.5, larger than 1.75, larger than 2.0, larger than 2.5, larger than 3.0, larger than 3.5, or larger than 4.0.

40. An optical fibre according to claim 7, 19, or 29 where those elongated elements having a refractive index being higher than a refractive index of any material adjacent to the elongated element comprise doped silica.

41. An optical fibre according to claim 1, 11, or 24, wherein the core region comprises a first additional elongated element extending in the longitudinal direction of the fibre.

42. An optical fibre according to claim 41, wherein the core region, in the cross section, is defined as the smallest rectangular area comprising all elements breaking the symmetry of the at least substantially two-dimensionally periodic structure, the smallest rectangular area defining a first main axis and a second main axis, the first and second main axes having a first and a second length, respectively, the first length being equal to the second length.

43. An optical fibre according to claim 41, wherein the core region, in the cross section, is defined as the smallest rectangular area comprising all elements breaking the symmetry of the at least substantially two-dimensionally periodic structure, the smallest rectangular area defining a first main axis and a second main axis, the first and second main axes having a first and a second length, respectively,
the first length being larger than a constant times the second length, said constant being larger than 1.1, larger than 1.2, larger than 1.5, larger than 2, larger than 5, larger than 10, larger than 20, larger than 30, larger than 40, or larger than 50.

44. An optical fibre according to claim 41, wherein the first additional element is a void, such as a void having a cross sectional area in the cross section being at least 0.5, at least one, at least 2, at least 3, at least 4, at least 5, at least 6, at least 7, at least 18, at least 36, or at least 72 times the cross sectional area of the unit cell.

45. An optical fibre according to claim 43, wherein the first additional element is adapted to hold a vacuum, a liquid or a gas.

46. An optical fibre according to claim 44, wherein the additional element or any material adjacent thereto comprises a dopant or a material showing higher order optical effects.

47. An optical fibre according to claim 41, wherein the core region comprises a second additional elongated element, the first and second additional elements being positioned at a distance where light travelling in and/or around one additional element is able to couple to the other additional element.

48. An optical fibre according to claim 47, wherein the second additional element is a void, the void being adapted to hold a liquid or gas.

49. An optical fibre according to claim 1, 11, or 24, the fibre comprising a plurality of core regions.

50. An optical fibre according to claim 49, wherein the core regions are positioned symmetrically within the periodic structure, a period of the core regions being larger than a period of the periodic structure.

51. A sensor for sensing or detecting at least one characteristic of a liquid or gas, the sensor comprising:
    a length of the optical fibre according to claim 1, 11 or 24, wherein the core region comprises at least a first additional element, the first element being a void extending along the longitudinal direction of the fibre,
    means for providing the liquid or gas into the void of the core region,
    means for introducing light into the core region, the light being adapted to interact with the gas or liquid in a manner so that the characteristic of the liquid or gas may be determined, and
    means for detecting light emitted from the fibre and for determining the characteristic of the liquid or gas.

52. A sensor according to claim 51, wherein the introducing means are adapted to introduce the light into the first additional element.

53. A sensor according to claim 51, wherein the core region comprises a second, elongated element extending in the longitudinal direction of the fibre, where the first and second additional elements are positioned at a distance where light travelling in one additional element is able to couple lo the other additional element, and wherein the introducing means are adapted to introduce the light into the second additional element.

54. A sensor according to any of claims 51–53, wherein at least part of an inner surface of the first additional element comprises a layer of a material being adapted to alter in response to the characteristic of the gas or liquid, and wherein the introducing means is adapted to introduce light of a wavelength responsive to the altering of the material.

55. A fibre amplifier for amplifying an optical signal, said fibre amplifier comprising:
    a length of optical fibre according to claim 1, 11, or 24, wherein the core region comprises a dopant material along at least part of the length, and
    means for providing pump radiation to the dopant material for pumping the dopant material so as to amplify the optical signal.

56. A fibre amplifier according to claim 55, further comprising means for spectrally separating the amplified optical signal from the pump signal.

57. A fibre amplifier according to claim 55, wherein the dopant comprises rare earth ions.

58. A fibre amplifier according to claim 57, wherein the rare earth ions are erbium.

59. A fibre amplifier according to claim 55, wherein the dopant comprises a photosensitive material.

60. A fibre amplifier according to claim 59, wherein the photosensitive material comprises germanium and/or deuterium.

61. A fibre laser for outputting laser radiation, said fibre laser comprising:
  a length of optical fibre according to claim 1, 11, or 24, wherein the core region comprises a dopant material along at least part of the length,
  means for providing pump radiation to the dopant material for pumping the dopant material so as to amplify the optical signal, and
  feedback means for selectively feeding back at least part of the amplified optical signal so as to repeatedly pass the amplified optical signal through the length of the optical fibre so as to further amplify the optical signal.

62. A fibre laser according to claim 61, wherein the dopant comprises rare earth ions.

63. A fibre laser according to claim 62, wherein the rare earth ions are erbium.

64. A fibre laser according to claim 61, wherein the dopant comprises a photosensitive material.

65. A fibre laser according to claim 64, wherein the photosensitive material comprises germanium and/or deuterium.

66. A preform for manufacturing an optical fibre, the preform having a length in a longitudinal direction and a cross section perpendicular thereto, the preform comprising:
  primary, elongated elements each having a centre axis extending in the longitudinal direction of the preform, the primary elements having a length in the longitudinal direction being essentially the same as the length of the preform,
  inserted elements each extending in the longitudinal direction of the preform over a length being smaller than the length of the preform,
  the primary, elongated elements and the inserted elements form both a non-periodic structure and an at least substantially two-dimensionally periodic structure, the non-periodic structure being surrounded by the substantially two-dimensionally periodic structure,
  the periodic structure being, in the cross-section perpendicular to the longitudinal direction, defined by at least one unit cell, wherein, for each unit cell:
  a first circle is defined as the largest circular area possible having a centre not positioned outside the unit cell and not enclosing any part of any primary elements, the periphery of said first circle defining an inserted element.

67. A preform according to claim 66, wherein the inserted elements, in at least part of the cross-section, defines a triangular structure.

68. A preform according to claim 66, wherein, for each unit cell, the centres of those primary, elongated elements, parts of which are within a distance of 1.5 or less, 1.2 or less, or 1.1 or less times the radius of the first circle from the centre of the first circle, define the vertices of a first polygon with three or more sides.

69. A preform according to claim 68, wherein the first polygon is a regular polygon.

70. A preform according to claim 68, wherein the first polygon has six or more sides, 12 or more sides, 18 or more sides, or 36 or more sides.

71. A preform according to claim 66, wherein a plurality of inserted elements are arranged along an axis extending in the longitudinal direction of the preform.

72. A preform according to claim 66, wherein at least part of the primary, elongated elements, in the cross-section, define a triangular structure, a Honeycomb structure, or a Kagomé structure.

73. A preform according to claim 66, wherein an outer surface of each of the primary, elongated elements define a primary area, and an outer surface of each of the inserted elements define a secondary area, wherein the area of any primary area is different from any secondary area.

74. A preform according to claim 73, wherein, for each unit cell, the sum of all secondary areas is larger than 0.09 times the area of that unit cell, larger than 0.1, larger than 0.15, larger than 0.2, larger than 0.25, larger than 0.3, larger than 0.4, larger than 0.5, larger than 0.6, larger than 0.7, or larger than 0.8 times the area of that unit cell.

75. A preform according to claim 74, wherein any secondary area is larger than a constant times any primary area, said constant being larger than 1.1, larger than 1.2, larger than 1.3, larger than 1.4, larger than 1.5, larger than 2, larger than 4, larger than 7, larger than 10, larger than 20, or larger than 50.

76. A preform according to claim 66, wherein the primary, elongated elements are hollow.

77. A preform according to claim 66, wherein the inserted, elongated elements are solid.

78. A preform according to claim 66, wherein any of the elongated elements comprise silica-based materials.

79. A preform according to claim 66, wherein any of the elongated elements comprise polymer-based materials.

80. A preform according to claim 66 further comprising further, elongated elements each having a centre axis extending in the longitudinal direction of the preform, and each having a centre not positioned outside the unit cell, and each having an area not exceeding the area of the unit cell, and each having a length in the longitudinal direction being essentially the same as the length of the preform, and each defining a further area being different from any area of primary, elongated elements.

81. A preform according to claim 80, wherein the further, elongated elements are solid.

82. A preform according to the claim 80, wherein at least part of the further, elongated elements, in the cross-section, are at least partly comprised within the first circle.

83. A preform according to claim 80, wherein the centres of at least part of the further, elongated elements, in the cross section, substantially coincide with the centre of the first circle.

84. A preform according to claim 66 further comprising a core region, the core region being defined as the non-periodic structure, the core region being surrounded by the at least substantially two-dimensionally periodic structure.

85. A preform according to claim 84, wherein the core region comprises a hollow region.

86. A preform according to claim 66 or 84 wherein the at least substantially two-dimensionally periodic structure surrounding the core region comprises at least two periods.

87. A method for fabricating a preform, the preform having a length in a longitudinal direction and a cross section perpendicular thereto, the method comprising the steps of:
  providing a holder for the preform, the holder having a predetermined shape and elongated grooves at its inner surface, the grooves having a length in the longitudinal direction being essentially the same as the length of the preform.
  providing primary, elongated elements each having a centre axis extending in the longitudinal direction of the preform, the primary elements having a length in the longitudinal direction being essentially the same as the length of the preform, providing secondary elements each extending in the longitudinal direction over a length being smaller than the length of the preform, and positioning a plurality of secondary elements at essentially the same position along the longitudinal direction of the preform.

88. An optical fibre with a waveguide structure having a longitudinal direction, said optical fibre comprising:

a cladding region extending along the longitudinal direction, said cladding region comprising an at least substantially two-dimensionally periodic structure comprising elongated elements each having a centre axis extending in the longitudinal direction of the waveguide, the elongated elements having a refractive index being lower than a refractive index of any material adjacent to the elongated elements, a core region extending along the longitudinal direction, said core region comprising at least one void extending along the longitudinal direction, a cross sectional area of said at least one void being larger than a constant times a cross sectional area of any elongated elements comprised within the cladding region, said constant being larger than 1.1, 1.3, 1.5, 1.7, 2, 3, 5, 10, 20, or 50.

89. An optical fibre according to claim 88, wherein:

a centre of a rectangle being defined as the centre of the smallest rectangular area possible, the centre being positioned not outside the core region, the rectangle enclosing the at least one void, a rectangularity is defined as the length of the longest side of the rectangle divided by the length of the shortest side of the rectangle, a first axis is defined as a longest vertice possible, the centre of the rectangle being positioned on said first axis, wherein each end of said first axis is enclosed within one of the at least one voids, a second axis is defined substantially perpendicular to the first axis, the second axis being defined as a longest vertice possible, the centre of the rectangle being positioned on said second axis, wherein each end of said first axis is enclosed within one of the at least one voids, and a eccentricity is being defined as the length of the first axis divided by the length of the second axis.

90. An optical fibre according to claim 88, wherein:

the rectangle is a square, wherein the eccentricity is larger than one, 1.1, 1.3, 1.5, 1.7, 2, 3, 5, or 10.

91. An optical fibre according to claim 88, wherein:

the rectangularity is larger than one, 1.1, 1.3, 1.5, 1.7, 2, 3, 5, or 10.

* * * * *